US011214535B2

(12) United States Patent
Bebensee et al.

(10) Patent No.: US 11,214,535 B2
(45) Date of Patent: *Jan. 4, 2022

(54) METHOD FOR PRODUCING ETHYLENEAMINES

(71) Applicant: BASF SE, Ludwigshafen am Rhein (DE)

(72) Inventors: Regine Helga Bebensee, Ludwigshafen am Rhein (DE); Thomas Heidemann, Ludwigshafen am Rhein (DE); Barbara Becker, Ludwigshafen am Rhein (DE); Eva Koch, Ludwigshafen am Rhein (DE); Hermann Luyken, Ludwigshafen am Rhein (DE); Johann-Peter Melder, Ludwigshafen am Rhein (DE)

(73) Assignee: BASF SE, Ludwigshafen am Rhein (DE)

(*) Notice: Subject to any disclaimer, the term of this patent is extended or adjusted under 35 U.S.C. 154(b) by 0 days.

This patent is subject to a terminal disclaimer.

(21) Appl. No.: 16/619,987

(22) PCT Filed: May 24, 2018

(86) PCT No.: PCT/EP2018/063589
§ 371 (c)(1),
(2) Date: Dec. 6, 2019

(87) PCT Pub. No.: WO2018/224315
PCT Pub. Date: Dec. 13, 2018

(65) Prior Publication Data
US 2020/0102262 A1    Apr. 2, 2020

(30) Foreign Application Priority Data
Jun. 9, 2017 (EP) .................................... 17175151

(51) Int. Cl.
| C07C 215/08 | (2006.01) |
| B01J 23/46 | (2006.01) |
| B01J 23/75 | (2006.01) |
| B01J 8/24 | (2006.01) |
| B01J 8/18 | (2006.01) |
| B01J 21/02 | (2006.01) |
| B01J 21/06 | (2006.01) |

(52) U.S. Cl.
CPC ........... *C07C 215/08* (2013.01); *B01J 8/1872* (2013.01); *B01J 8/24* (2013.01); *B01J 23/462* (2013.01); *B01J 23/75* (2013.01); *B01J 21/02* (2013.01); *B01J 21/066* (2013.01)

(58) Field of Classification Search
CPC .. C07C 209/16; C07C 215/08; B01J 23/8913; B01J 35/026; B01J 23/462; B01J 23/75; B01J 8/1872; B01J 8/24
See application file for complete search history.

(56) References Cited

U.S. PATENT DOCUMENTS

| 3,137,730 A | 6/1964 | Fitz-William |
| 3,270,059 A | 8/1966 | Winderl et al. |
| 4,111,840 A | 9/1978 | Best |
| 4,701,434 A | 10/1987 | Köll |
| 4,855,505 A | 8/1989 | Köll |
| 5,958,825 A * | 9/1999 | Wulff-Doring ...... B01J 23/8926 502/300 |
| 6,525,222 B2 | 2/2003 | Nouwen et al. |
| 7,405,327 B2 | 7/2008 | Haese et al. |
| 7,700,806 B2 | 4/2010 | van Cauwenberge et al. |
| 7,919,655 B2 | 4/2011 | Kubanek et al. |
| 8,063,252 B2 | 11/2011 | Kubanek et al. |
| 8,268,995 B2 | 9/2012 | Kubanek et al. |

(Continued)

FOREIGN PATENT DOCUMENTS

| CN | 102190588 A | 9/2011 |
| CN | 102233272 | 11/2011 |

(Continued)

OTHER PUBLICATIONS

U.S. Appl. No. 16/620,023, Dec. 2019, Bebensee et al.*
Hu et al. ACS Catalysis, (2015), V.5, p. 6069-6077.*
International Preliminary Examination Report for PCT/EP2018/063589 dated May 22, 2019.
International Preliminary Examination Report for PCT/EP2018/063591 dated Aug. 28, 2019.

(Continued)

*Primary Examiner* — Yong L Chu
(74) *Attorney, Agent, or Firm* — Faegre Drinker Biddle & Reath LLP

(57) ABSTRACT

The invention relates to processes for preparing alkanolamines and ethyleneamines in the liquid phase, by reacting ethylene glycol and/or monoethanolamine with ammonia in the presence of an amination catalyst comprising one or more active metals selected from Sn and the elements of groups 8, 9, 10 and 11 of the Periodic Table of the Elements, wherein the amination catalyst is obtained by reductive calcination of a catalyst precursor. The catalyst precursor here is preferably prepared by contacting a conventional or catalytic support material with one or more soluble compounds of the active metals and optionally one or more soluble compounds of added catalyst elements. The present invention further relates to a process for preparing an amination catalyst comprising one or more active metals selected from Sn and the elements of groups 8, 9, 10 and 11 of the Periodic Table of the Elements, the amination catalyst being obtained by reductive calcination of a catalyst precursor, wherein the reactor in which the catalyst precursor is reductively calcined is connected to a denox plant, and to the use of a denox plant in the preparation of amination catalysts.

20 Claims, No Drawings

(56) References Cited

U.S. PATENT DOCUMENTS

| | | |
|---|---|---|
| 8,293,945 B2 | 10/2012 | Kubanek et al. |
| 8,318,982 B2 | 11/2012 | Kubanek et al. |
| 8,324,430 B2 | 12/2012 | Kubanek et al. |
| 8,487,135 B2 | 7/2013 | Kubanek et al. |
| 9,019,075 B2 | 4/2015 | Hayashida |
| 9,174,201 B2 | 11/2015 | Ernst et al. |
| 2020/0131111 A1* | 4/2020 | Heidemann .......... B01J 37/0203 |

FOREIGN PATENT DOCUMENTS

| | | | |
|---|---|---|---|
| CN | 102233272 A | 11/2011 | |
| DE | 1172268 B | 6/1964 | |
| EP | 198699 A2 | 10/1986 | |
| EP | 0839575 A2 | 5/1998 | |
| EP | 1106600 A2 | 6/2001 | |
| EP | 2780109 A1 * | 9/2014 | .......... C07C 229/76 |
| WO | WO-96/38226 A1 | 12/1996 | |
| WO | WO-00/06749 A2 | 2/2000 | |
| WO | WO-2005110969 A1 | 11/2005 | |
| WO | WO-2007093514 A1 | 8/2007 | |
| WO | WO-2008006749 A1 | 1/2008 | |
| WO | WO-2008006750 A1 | 1/2008 | |
| WO | WO-2009/008051 A1 | 1/2009 | |
| WO | WO-2009080506 A1 | 7/2009 | |
| WO | WO-2009080508 A1 | 7/2009 | |
| WO | WO-2009080510 A1 | 7/2009 | |
| WO | WO-2010031719 A1 | 3/2010 | |
| WO | WO-2011067199 A1 | 6/2011 | |
| WO | WO-2011067200 A1 | 6/2011 | |
| WO | WO-201 3072289 A1 | 5/2013 | |

OTHER PUBLICATIONS

International Preliminary Examination Report for PCT/EP2018/063613 dated Aug. 28, 2019.
International Search Report for PCT/EP2018/063589 dated Oct. 8, 2018.
International Search Report for PCT/EP2018/063591 dated Aug. 8, 2018.
International Search Report for PCT/EP2018/063613 dated Aug. 8, 2018.
U.S. Appl. No. 16/619,976, filed Dec. 6, 2019.
U.S. Appl. No. 16/620,023, filed Dec. 6, 2019.
"BASF: The Right Choice for Nitric Acid Plants", BASF Technical Note, 2012, pp. 1-12.
European Search Report for EP Patent Application No. 17175151.4, dated Oct. 23, 2017, 03 pages.

* cited by examiner

METHOD FOR PRODUCING ETHYLENEAMINES

CROSS-REFERENCE TO RELATED APPLICATIONS

This application is a national stage application (under 35 U.S.C. § 371) of PCT/EP2018/063589, filed. May 24, 2018, which claims benefit of European Application No. 17175151.4, filed Jun. 9, 2017, both of which are incorporated herein by reference in their entirety.

The present invention relates to a process for preparing alkanolamines and ethyleneamines, especially ethylenediamine. The present invention further relates to a process for preparing amination catalysts.

Two processes are generally employed for industrial scale preparation of ethylenediamine (EDA).

Firstly, EDA can be prepared by reaction of 1,2-dichloroethane with ammonia with elimination of HCl (EDC process). A further industrial scale process for preparation of EDA is the reaction of monoethanolamine (MEA) with ammonia in the presence of amination catalysts (MEA process).

As an alternative to the established processes, EDA can also be prepared by reaction of monoethylene glycol (MEG) with ammonia.

Such a process would have various advantages. One advantage is the good availability of MEG compared to MEA.

MEA is prepared on the industrial scale by reaction of ethylene oxide (EO) and ammonia. What is generally formed is a reaction mixture comprising, as well as MEA, also higher ethanolamines such as diethanolamine (DEOA) and triethanolamine (TEOA). These by-products have to be separated from MEA by a separate distillation step. Ethylene oxide is a highly flammable gas that can form explosive mixtures with air. The handling of EO is correspondingly complex. The preparation of MEA thus requires a technically complex EO plant with downstream purifying distillation.

By contrast, MEG can be produced either on the basis of petrochemical raw materials or on the basis of renewable raw materials. By petrochemical means, MEG is likewise prepared from EO by reaction with water. In the same way as in the reaction of EO with ammonia, it is not possible in the reaction of EO with water to prevent MEG that has already formed from reacting with EO to give by-products such as di- and triethylene glycol. The selectivity for MEG is about 90% and is thus, however, distinctly higher than the selectivity for MEA, which is generally 70-80%. The Shell omega process once again distinctly increased the selectivity for MEG—to about 99%. In the omega process, EO is reacted with $CO_2$ to give ethylene carbonate which, in the second step, is selectively hydrolyzed to MEG.

MEG can also be prepared via the synthesis gas route, for example by oxidative carbonylation of methanol to give dimethyl oxalate and subsequent hydrogenation thereof. Thus, a further possible petrochemical raw material for the preparation of MEG is also natural gas or coal. Alternatively, MEG can also be prepared from renewable raw materials, such as corn or sugarcane, by fermentation to ethanol, followed by dehydration to ethene and subsequent reaction with oxygen to give ethylene oxide.

Owing to the many production variants, the availability of MEG is generally high, which generally has a positive effect on raw material costs.

The prior art discloses that the reaction of MEG with ammonia to give EDA can be effected either in the liquid phase or in the gas phase.

The amination of MEG in the gas phase is disclosed in the two Chinese applications CN 102 190588 and CN 102233272.

For instance, CN 102190588 describes the one-stage conversion of MEG and ammonia in the presence of Cu catalysts. According to the description, the reaction pressure is within a range from 3 to 30 bar. The reaction temperature is in the range from 150 to 350° C.

Application CN 102233272 discloses the reaction of MEG with ammonia in the gas phase over catalysts that include Cu and Ni as main constituents and Zr, Zn, Al, Ti, Mn and Ce as secondary component. However, the composition of the reaction mixtures obtained was not disclosed.

As an alternative to conversion in the gas phase, the reaction of MEG with ammonia and hydrogen can also be effected in the liquid phase. However, there is generally a considerable difference in the reaction characteristics of catalysts in the gas phase and liquid phase, and so it is generally impermissible to apply conclusions from the reaction characteristics of MEG in the gas phase to the reaction characteristics of MEG in the liquid phase.

An overview of the metal-catalyzed amination of MEG in the liquid phase is given in the Diplom thesis "Reaktionskinetische Untersuchungen zur metallkatalysierten Aminierung von Ethylenglykol in der flüssigen Phase" [Studies of Reaction Kinetics of the Metal-Catalyzed Amination of Ethylene Glycol in the Liquid Phase] by Carsten Wolfgang Ihmels ("Reaktionskinetische Untersuchungen zur metallkatalysierten Aminierung von Ethylenglykol in der flüssigen Phase", Diplom thesis from the Carl von Ossietzky University of Oldenburg dated May 17, 2000). Ihmels describes a multitude of further reactions and side reactions that can occur in the amination of MEG, for example the formation of di- and triethanolamine, disproportionation, nitrile formation, carbonyl condensation and fragmentation reactions. Condensation and disproportionation in the case of dihydric alcohols can ultimately also lead to the formation of oligomers, such as diethylenetriamine (DETA), triethylenetetramine (TETA) and polymers. An important further side reaction is cyclization. For instance, diethanolamine or DETA can react further to give piperazine (PIP). Higher temperatures promote dehydrogenation, which follows on from the cyclization, to give aromatics. Thus, the reaction of MEG with ammonia gives a broad product spectrum, some products in the product spectrum being of greater commercial interest than others. For instance, the commercial demand for EDA, DETA and TETA is higher than that for PIP or aminoethylethanolamine (AEEA). The object of many studies in the reaction of MEG with ammonia was therefore to find catalysts and reaction conditions that lead to an advantageous product spectrum.

Ihmels himself studied the conversion of MEG over supported cobalt/silicon dioxide catalysts. Amination to give the desired MEA and EDA target product was unsuccessful. Instead, high-polymeric reaction products were formed. Under milder conditions, still with incomplete conversion of MEG, the target products MEA and EDA were obtained in low yields. The main products were oligomeric compounds.

U.S. Pat. No. 4,111,840 discloses the reaction of MEG with ammonia and hydrogen at pressures of 500 to 5000 psig (about 34 to 340 bar) over supported Ni/Re catalysts. Before the reduction, the catalysts are calcined in the range from 300 to 500° C. It is disclosed that the calcination can be conducted under an inert atmosphere.

U.S. Pat. No. 3,137,730 discloses the reaction of MEG with ammonia in the liquid phase at temperatures of 200-300° C. and pressures above 1000 psig (about 69 bar) over Cu/Ni catalysts. In the examples, the catalysts are calcined at temperatures of 400 to 800° C.

DE 1172268 discloses the conversion of ethylene glycol over catalysts comprising at least one of the metals Cu, Ag, Mn, Fe, Ni and Co. In one example, MEG was reacted with ammonia at 180° C. and a pressure of 300 bar in the presence of hydrogen over a Co catalyst. The catalysts are prepared by sintering, appropriately above 700° C.

WO 2007/093514 discloses a two-stage process for preparing EDA, wherein, in the first process stage, the amination is conducted over a hydroamination catalyst up to an MEA conversion of not more than 40% and, in the second process stage, a supported shaped Ru/Co catalyst body having small geometry is used and the second stage is conducted at a temperature at least 10° C. higher than the first process stage. The catalysts are calcined at 200 to 500° C. In the examples, the calcination is effected in the presence of air.

WO 2013072289 discloses the reaction of alcohols with a nitrogen compound over catalysts that include the element Sn in addition to Al, Cu, Ni and Co. Preferred alcohols mentioned are ethylene glycol and monoethanolamine. The calcination is generally effected at temperatures in the range from 300 to 800° C. In one example, air is passed through the calcination.

Catalysts for the amination of alcohols that comprise Sn are likewise disclosed in WO 2011067200. The catalysts described therein comprise not only Sn but also the elements Co, Ni, Al and Cu. The calcination is generally effected at temperatures in the range from 300 to 800° C.

Further catalysts for the amination of alcohols are disclosed in WO 200908051, WO 2009080508, WO 200006749 and WO 20008006750. The catalysts comprise not only Zr and Ni but also Cu, Sn, Co and/or Fe. Further constituents are elements such as V, Nb, S, O, La, B, W, Pb, Sb, Bi and In.

WO 96/38226 discloses catalysts for the amination of alcohols that comprise Re, Ni, Co, B, Cu and/or Ru. In one example, a support of SiO2 is impregnated with a solution of NH4ReO4, Ni nitrate, H3BO3, Co nitrate and Cu nitrate and then calcined. In a further impregnation step, the calcined and impregnated support is impregnated with Ru chloride. Before the reduction, a calcination is optionally conducted in the range from 200 to 500° C., the calcination preferably being effected in the presence of air in accordance with the disclosure.

U.S. Pat. Nos. 4,701,434 and 4,855,505 disclose the amination of MEG and MEA in the presence of catalysts comprising Ni and/or Co and Ru. This involves contacting a catalyst precursor comprising Ni oxide and/or Co oxide with an Ru halide, for example Ru chloride, and then reducing it in a hydrogen stream. According to the disclosure, the calcination of the catalyst precursors is effected at 300 to 600° C. in an air stream. The subsequent reduction of the catalyst precursor treated with Ru halide is effected in two stages, first by reduction at 150 to 300° C. and by increasing the temperature to 300 to 600° C. in a second stage.

EP 0839575 discloses catalysts comprising Co, Ni and mixtures thereof and Ru on a porous metal oxide support. The catalysts are prepared by impregnating the support with the metals, drying and calcining the impregnated support and reducing the calcined support in a hydrogen stream. It is further disclosed that the support can be impregnated with metal compounds in any sequence. In one example, a support is first impregnated with a solution of Ni nitrates, Co nitrates and Cu nitrates, then calcined and further impregnated with an aqueous Ru nitrate solution and calcined again at 400° C.

U.S. Pat. No. 5,958,825 discloses catalysts comprising Ni and Co and Ru which are prepared by impregnating a support material and subsequent drying and calcination of the impregnated catalyst. In example 1 of U.S. Pat. No. 5,958,825, an aluminum oxide support is first impregnated with NiO, CoO and CuO and, after a calcination at 400° C., the catalyst precursor was sprayed with an Ru nitrate solution. The catalyst precursor obtained in this way was dried and calcined at 400° C.

It was an object of the present invention to develop a heterogeneous catalyst for the amination of MEG and/or MEA in the liquid phase that shows adequate activity and selectivity in the conversion of MEG to MEA and/or EDA.

More particularly, the formation of products of value, i.e. those ethanolamines or ethyleneamines with a high commercial significance, especially MEA and EDA, was to be promoted and the formation of cyclic ethyleneamines, especially PIP, and higher ethanolamines, especially AEEA, was to be kept low since the commercial demand for PIP or AEEA is lower than for EDA and MEA.

More particularly, the concentration of particular unwanted by-products, such as NMEDA, NEEDA and ethylamine (EA), was also to be reduced. NMEDA has a volatility that barely differs from EDA, and so the two components are separable only with high separation complexity. It would thus be advantageous if only small amounts of NMEDA were to be formed even in the production. The customary product specifications of EDA require that less than 500 ppm of NMEDA be present in EDA.

In addition, the catalysts were also to have high activity and enable high MEG conversion in order to achieve a good space-time yield.

Overall, a good spectrum of properties in relation to overall selectivity, selectivity quotient and the formation of unwanted by-products was thus to be achieved.

The object of the present invention was achieved by a process for preparing alkanolamines and ethyleneamines in the liquid phase, by reacting ethylene glycol and/or monoethanolamine with ammonia in the presence of an amination catalyst comprising one or more active metals selected from Sn and the elements of groups 8, 9, 10 and 11 of the Periodic Table of the Elements, wherein the amination catalyst is obtained by reductive calcination of a catalyst precursor.

It has been found that, surprisingly, amination catalysts that are reductively calcined in accordance with the invention have high selectivity for the linear amination products MEA and EDA in the reaction of MEG with NH3, while the selectivity for the cyclic amination product PIP and the higher ethanolamine AEEA is low.

In addition, it has been found that catalysts of the invention form a lower level of unwanted by-products, such as NMEDA. Moreover, it has been found that the amination catalysts used in the process of the invention have a high activity for the conversion of MEG and hence enable high space-time yields in the conversion.

In the preparation of the amination catalysts by reductive calcination that are suitable for use in the reaction of the invention, the reductive calcination of the catalyst precursors can give rise to nitrogen oxides that can form explosive mixtures. Nitrogen oxides can form especially when, in the preparation of catalyst precursors, a catalytic or noncatalytic support material has been contacted with nitrates or nitrosylnitrates of the active metals or added catalyst elements during the preparation.

It was therefore also an object of the present invention to provide a process for preparing amination catalysts that meets high safety standards.

The object was achieved by a process for preparing an amination catalyst comprising one or more active metals selected from Sn and the elements of groups 8, 9, 10 and 11 of the Periodic Table of the Elements, the amination catalyst being obtained by reductive calcination of a catalyst precursor, wherein the reactor in which the catalyst precursor is reductively calcined is connected to a denox plant.

The following abbreviations are used above and hereinafter:
AEEA: aminoethylethanolamine
AEP: aminoethylpiperazine
DETA: diethylenetriamine
EA: ethylamine
EDA: ethylenediamine
EO: ethylene oxide
EDC: ethylene dichloride
HEP: hydroxyethylpiperazine
NEEDA: N-ethylethylenediamine
NMEDA: N-methylethylenediamine
MEA: monoethanolamine
MEG: monoethylene glycol
PEHA: pentaethylenehexamine
PIP: piperazine
TEPA: tetraethylenepentamine
TETA: triethylenetetramine Amination Catalysts The process of the invention for preparing alkanolamines and ethyleneamines by reaction of MEG and/or MEA with $NH_3$ is effected in the presence of amination catalysts.

Catalyst Precursors

The amination catalysts are obtained by reductive calcination of catalyst precursors.

Active Composition

The catalyst precursors used comprise an active composition.

The active composition of the catalyst precursors comprises active metals and optionally one or more added catalyst elements, and also optionally one or more support materials.

Active Metals

The active composition of the catalyst precursor comprises one or more active metals selected from the group consisting of Sn and the elements of groups 8, 9, 10 and 11 of the Periodic Table of the Elements.

Preferably, the active composition of the catalyst precursor comprises one or more active metals selected from the group consisting of Fe, Ru, Co, Ni, Cu and Sn.

Most preferably, the active composition of the catalyst precursor comprises one or more active metals selected from the group consisting of Ru, Co, Ni, Cu and Sn.

In a particularly preferred embodiment, one of the one or more active metals is Ru or Co.

In a very particularly preferred embodiment, one of the one or more active metals is Ru.

In further very particularly preferred embodiments, the amination catalyst comprises one of the following combinations of the active metals:
Ru and Co;
Ru and Sn;
Ru and Cu;
Ru and Ni;
Ru and Co and Sn;
Ru and Co and Cu;
Ru and Co and Ni;
Ru and Sn and Cu;
Ru and Sn and Ni;
Ru and Cu and Ni;
Ru and Co and Sn and Cu;
Ru and Co and Sn and Ni;
Ru and Co and Sn and Cu and Ni;
Co and Sn;
Co and Cu;
Co and Ni;
Co and Sn and Cu;
Co and Sn and Ni;
Co and Cu and Ni; or
Co and Sn and Cu and Ni;

In a very particularly preferred embodiment, the amination catalyst comprises one of the following combinations comprising both Ru and Co:
Ru and Co;
Ru and Co and Sn;
Ru and Co and Cu;
Ru and Co and Ni;
Ru and Co and Sn and Cu;
Ru and Co and Sn and Ni;
Ru and Co and Sn and Cu and Ni.

Added Catalyst Elements

The active composition of the catalyst precursors used in the process of the invention may optionally comprise one or more added catalyst elements.

The added catalyst elements are metals or semimetals selected from groups 1 to 17 of the Periodic Table (excluding the active metals), the element P and the rare earth metals.

Preferred added catalyst elements are Zr, Al, Pb, Bi, Ce, Y, and Mn.

Particularly preferred added catalyst elements are Zr, Al, and Mn.

Very particularly preferred added catalyst elements are Zr and Al.

Catalytically Active Components

In the catalyst precursor, the active metals and the added catalyst elements are generally in the form of their oxygen compounds, for example of carbonates, oxides, mixed oxides or hydroxides of the added catalyst elements or active metals.

The oxygen compounds of the active metals and of the added catalyst elements are referred to hereinafter as catalytically active components.

However, the term "catalytically active components" is not intended to imply that these compounds are already catalytically active per se. The catalytically active components generally have catalytic activity in the inventive conversion only after reduction of the catalyst precursor.

In general, the catalytically active components are converted to the catalytically active components by a calcination from soluble compounds of the active metals or of the added catalyst elements or precipitates of the active metals or of the added catalyst elements, the conversion generally being effected by dewatering and/or decomposition.

Support Materials

The catalytically active composition may further comprise one or more support materials.

In the context of the present invention, a distinction is made between catalytic support materials and conventional support materials.

Conventional Support Materials

The conventional support materials are generally added catalyst elements which are used in solid form in the preparation of the catalyst precursors and onto which the soluble compounds of the active metals and/or added catalyst elements are precipitated or which are impregnated with the soluble compounds of the active metals or added catalyst elements. In general, conventional support materials are solids having a high surface area.

The conventional support material used may be the added catalyst element carbon, for example in the form of graphite, carbon black and/or activated carbon.

Preferred conventional support materials are oxides of the added catalyst elements Al, Ti, Zn, Zr and Si or mixtures thereof, for example aluminum oxide (gamma, delta, theta, alpha, kappa, chi or mixtures thereof), titanium dioxide (anatase, rutile, brookite or mixtures thereof), zinc oxide, zirconium dioxide, silicon dioxide (such as silica, fumed silica, silica gel or silicates), aluminosilicates, minerals, such as hydrotalcite, chrysotile and sepiolite.

Particularly preferred support materials are aluminum oxide or zirconium oxide or mixtures thereof.

In a particularly preferred embodiment, the conventional support material is aluminum oxide; zinc oxide or a mixture thereof with a median diameter of the particles $d_{50}$ in the range from 50 to 2000 μm, preferably 100 to 1000 μm and more preferably 300 to 700 μm. In a particularly preferred embodiment, the median diameter $d_{50}$ of the particles is in the range from 1 to 500 μm, preferably 3 to 400 μm and more preferably 5 to 300 μm. In the preferred working examples, the standard deviation of the particle diameter is generally in the range from 5% to 200%, preferably 10% to 100% and especially preferably 20% to 80% of the median diameter $d_{50}$.

Catalytic Support Materials

In a very particularly preferred embodiment, the support material is a catalytic support material. A catalytic support material is a solid comprising one or more active metals. Catalytic support materials are especially compounds which, as described hereinafter, are by themselves prepared by coprecipitation, precipitative application or impregnation and then generally worked up by separating off, washing, drying and calcining and optionally converted to the desired shape and geometry specified below by a shaping step.

Preparation of Catalytic Support Materials

Catalytic support materials can be prepared by known processes, for example by precipitation reactions (e.g. coprecipitation or precipitative application) or impregnation.

Catalytic support materials can be prepared via a coprecipitation of soluble compounds of the active metals or added catalyst elements with a precipitant. For this purpose, one or more soluble compounds of the corresponding active metals and optionally one or more soluble compounds of the added catalyst elements in a liquid is admixed with a precipitant while heating and stirring until the precipitation is complete.

The liquid used is generally water.

Useful soluble compounds of the active metals typically include the corresponding metal salts, such as the nitrates or nitrosylnitrates, chlorides, sulfates, carboxylates, especially the acetates, or nitrates or nitrosylnitrates, of the aforementioned metals.

The soluble compounds of the added catalyst elements that are used are generally water-soluble compounds of the added catalyst elements, for example the water-soluble nitrates or nitrosylnitrates, chlorides, sulfates, carboxylates, especially the acetate or nitrates or nitrosylnitrates.

Catalytic support materials can also be prepared by precipitative application.

Precipitative application is understood to mean a preparation method in which generally one or more support materials, preferably conventional support materials, are suspended in a liquid and then soluble compounds of the active metals, such as soluble metal salts of the active metals, and optionally soluble compounds of the added catalyst elements are added, and these are then applied by precipitative application to the suspended support material by addition of a precipitant (described, for example, in EP-A2-1106600, page 4, and A. B. Stiles, Catalyst Manufacture, Marcel Dekker, Inc., 1983, page 15).

The soluble compounds of the active metals or added catalyst elements that are used are generally water-soluble compounds of the active metals or added catalyst elements, for example the water-soluble nitrates or nitrosylnitrates, chlorides, sulfates, carboxylates, especially the acetate or nitrates or nitrosylnitrates.

The support materials that are used in the precipitative application may be used, for example, in the form of spall, powders or shaped bodies, such as strands, tablets, spheres or rings.

Preference is given to using support materials that already have the preferred shape and geometry of the shaped bodies described hereinafter (see section "Shape and geometry of the support materials").

Typically, in the precipitation reactions, the soluble compounds of the active metals or added catalyst elements are precipitated as sparingly soluble or insoluble, basic salts by addition of a precipitant.

The precipitants used are preferably alkalis, especially mineral bases, such as alkali metal bases. Examples of precipitants are sodium carbonate, sodium hydroxide, potassium carbonate or potassium hydroxide.

The precipitants used may also be ammonium salts, for example ammonium halides, ammonium carbonate, ammonium hydroxide or ammonium carboxylates.

The precipitation reactions can be conducted, for example, at temperatures of 20 to 100° C., particularly 30 to 90° C., especially at 50 to 70° C.

The precipitates obtained in the precipitation reactions are generally chemically inhomogeneous and generally comprise mixtures of the oxides, oxide hydrates, hydroxides, carbonates and/or hydrogencarbonates of the metals or semimetals used. With regard to the filterability of the precipitates, it may prove to be favorable for them to be aged—meaning that they are left to themselves for a certain time after precipitation, optionally under hot conditions or with air being passed through.

The catalytic support materials can also be prepared by impregnating support materials with soluble compounds of the active metals or added catalyst elements (impregnation).

The support materials that are used in the impregnation may be used, for example, in the form of spall, powders or shaped bodies, such as strands, tablets, spheres or rings. Preference is given to using support materials that already have the preferred shape and geometry of the shaped bodies described hereinafter (see section "Shape and geometry of the support materials").

The abovementioned support materials can be impregnated by the customary processes (A. B. Stiles, Catalyst Manufacture—Laboratory and Commercial Preparations, Marcel Dekker, New York, 1983), for example by applying a salt of the active metals or added catalyst elements in one or more impregnation stages.

Useful salts of the active metals or of the added catalyst elements generally include water-soluble salts such as the carbonates, nitrates or nitrosylnitrates, carboxylates, especially the nitrates or nitrosylnitrates, acetates or chlorides, of the corresponding active metals or added catalyst elements, which are generally converted at least partly to the corresponding oxides or mixed oxides under the conditions of the calcination.

The impregnation can also be effected by the "incipient wetness method", in which the support material is moistened with the impregnation solution up to a maximum of saturation, according to its water absorption capacity, or the support material is sprayed with the impregnation solution. Alternatively, impregnation may take place in supernatant solution.

In the case of multistage impregnation processes, it is appropriate to dry and optionally to calcine between individual impregnation steps. Multistage impregnation should be employed advantageously when the support material is to be contacted with salts in a relatively large amount.

For application of multiple active metals and/or added catalyst elements and/or basic elements to the support material, the impregnation can be effected simultaneously with all salts or in any sequence of the individual salts in succession.

Workup of the Catalytic Support Materials

The impregnated catalytic support materials obtained by these impregnation methods or the precipitates obtained by the precipitation methods are typically processed by separating them from the liquid in which the impregnation or precipitation has been conducted, and washing, drying, calcining and optionally conditioning and subjecting them to a shaping process.

Separation and Washing

After the preparation of the catalytic support materials, the precipitates thus obtained or impregnated, conventional support materials are generally separated from the liquid in which the catalytic support materials were prepared and washed.

Processes for separating and washing the catalytic support materials are known, for example, from the article "Heterogeneous Catalysis and Solid Catalysts, 2. Development and Types of Solid Catalysts", in Ullmann's Encyclopedia of Industrial Chemistry (DOI: 10.1002/14356007.o05_o02).

The wash liquid used is generally a liquid in which the separated catalytic support material is sparingly soluble but which is a good solvent for impurities adhering to the catalyst, for example precipitant. A preferred wash liquid is water.

In batch preparation, the separation is generally effected with frame filter presses. The washing of the filter residue with wash liquid can be effected here by passing the wash liquid in countercurrent direction to the filtration direction.

In continuous preparation, the separation is generally effected with rotary drum vacuum filters. The washing of the filter residue is typically effected by spraying the filter residue with the wash liquid.

The catalytic support material can also be separated off by centrifugation. In general, the washing here is effected by adding wash liquid in the course of centrifuging.

Drying

The catalytic support material separated off is generally dried.

Processes for drying the catalytic support materials are known, for example, from the article "Heterogenous Catalysis and Solid Catalysts, 2. Development and Types of Solid Catalysts", in Ullmann's Encyclopedia of Industrial Chemistry (DOI10.1002/14356007.o05_o02).

The drying is effected here at temperatures in the range from preferably 60 to 200° C., especially from 80 to 160° C. and more preferably from 100 to 140° C., where the drying time is preferably 6 h or more, for example in the range from 6 to 24 h. However, depending on the moisture content of the material to be dried, shorter drying times, for example about 1, 2, 3, 4 or 5 h, are also possible.

The washed catalytic support materials that have been separated off can be dried, for example, in chamber ovens, drum driers, rotary kilns or belt driers.

The catalytic support materials can also be dried by spray-drying a suspension of the catalytic support material.

Calcination

In general, the catalytic support materials are calcined after the drying.

During the calcination, thermally labile compounds of the active metals or added catalyst elements, such as carbonates, hydrogencarbonates, nitrates or nitrosylnitrates, chlorides, carboxylates, oxide hydrates or hydroxides, are at least partly converted to the corresponding oxides and/or mixed oxides.

The calcination is generally effected at a temperature in the range from 250 to 1200° C., preferably 300 to 1100° C. and especially from 500 to 1000° C.

The calcination can be effected under any suitable gas atmosphere, preference being given to air and/or air mixtures, such as lean air. The calcination can alternatively be effected in the presence of hydrogen, nitrogen, helium, argon and/or steam or mixtures thereof.

The calcination is generally effected in a muffle furnace, a rotary kiln and/or a tunnel kiln, the calcination time preferably being 1 h or more, more preferably in the range from 1 to 24 h and most preferably in the range from 2 to 12 h.

Composition of the Catalytic Support Materials

The composition of the catalytic support materials can be measured by means of known methods of elemental analysis, for example of atomic absorption spectrometry (AAS), of atomic emission spectrometry (AES), of X-ray fluorescence analysis (XFA) or of ICP-OES (Inductively Coupled Plasma Optical Emission Spectrometry).

The concentration figures (in % by weight) of the catalytically active components in the context of the present invention are reported as the corresponding oxide.

The added catalyst elements of group 1 (alkali metals) are calculated as $M_2O$, for example $Na_2O$.

The added catalyst elements of group 2 (alkaline earth metals) are calculated as MO, for example MgO or CaO.

The added catalyst elements of group 13 (boron group) are calculated $M_2O_3$, for example $B_2O_3$ or $Al_2O_3$.

In the carbon group (group 14), Si is calculated as $SiO_2$, Ge as GeO, Sn as SnO and Pb as PbO.

In the nitrogen group (group 15), P is calculated as $H_3PO_4$, As as $As_2O_3$, Sb as $Sb_2O_3$ and Bi as $Bi_2O$.

In the group of the chalcogens (group 16), Se is calculated as $SeO_2$ and Te as $TeO_2$.

In the scandium group (group 3), Sc is calculated as $Sc_2O_3$, Y as $Y_2O_3$ and La as $La_2O_3$.

In the titanium group (group 4), Ti is calculated as $TiO_2$, Zr as $ZrO_2$ and Hf as $HfO_2$.

In the vanadium group (group 5), V is calculated as $V_2O_5$, Nb as $Nb_2O_5$ and Ta as $Ta_2O_5$.

In the chromium group (group 6), Cr is calculated as $CrO_2$, Mo as $MoO_3$ and W as $WO_2$.

In the manganese group (group 7), Mn is calculated as $MnO_2$ and Re as $Re_2O_7$.

In the iron group (group 8), Fe is calculated as $Fe_2O_3$, Ru as $RuO_2$ and Os as $OsO_4$.

In the cobalt group (group 9), Co is calculated as CoO, Rh as $RhO_2$ and Ir as $IrO_2$.

In the nickel group (group 10), Ni is calculated as NiO, Pd as PdO and Pt as PtO.

In the copper group (group 11), Cu is calculated as CuO, Ag as AgO and Au as $Au_2O_3$.

In the zinc group (group 12), Zn is calculated as ZnO, Cd as CdO and Hg as HgO.

The concentration figures (in % by weight) of the components of the catalytic support material are each based—unless stated otherwise—on the total mass of the catalytic support material after the last calcination.

The composition of the catalytic support materials is generally dependent on the preparation method described hereinafter (coprecipitation or precipitative application or impregnation).

The catalytic support materials preferably consist solely of catalytically active components of the active metals or added catalyst elements, for example in the form of a conventional support material, and optionally a forming auxiliary (for example graphite or stearic acid) if the catalytic support material is used in the form of a shaped body.

The proportion of the catalytically active components of the active metals or added catalyst elements, based on the total mass of the catalytic support material, is typically 70% to 100% by weight, preferably 80% to 100% by weight, more preferably 90% to 100% by weight, even more preferably 95% by weight to 100% by weight and especially preferably 97% by weight to 100% by weight.

Catalytic support materials that are prepared by coprecipitation do not comprise any conventional support material. If the precipitation, as described hereinafter, is effected in the presence of a conventional support material, the preparation method for catalytic support materials is referred to in the context of the present invention as precipitative application.

Catalytic support materials that are prepared by coprecipitation comprise generally 1 to 3, more preferably 1 to 2 and especially preferably 1 active metal(s).

Irrespective of the number of active metals present in the active composition, in the case of catalytic support materials that are prepared by coprecipitation, the composition of the catalytically active components of the active metals is preferably in the range from 1% to 95% by weight, more preferably 10% to 90% by weight, even more preferably 20% to 85% by weight and especially preferably 50% to 80% by weight, based on the total mass of the catalytic support material, and where the catalytically active components are calculated as the oxide.

Catalytic support materials that are prepared by coprecipitation comprise generally 1 to 5, more preferably 1 to 4 and especially preferably 1 to 3 different added catalyst elements.

Irrespective of the number of added catalyst elements present in the active composition, in the case of catalytic support materials that are prepared by coprecipitation, the composition of the catalytically active components of the added catalyst elements is preferably in the range from 1% to 90% by weight, more preferably 5% to 80% by weight and most preferably 10% to 60% by weight, based on the total mass of the catalytic support material, and where the catalytically active components are calculated as the oxide.

Catalytic support materials that are prepared by precipitative application comprise generally 5% to 95% by weight, preferably 10% to 80% by weight and more preferably 15% to 60% by weight of conventional support material.

Catalytic support materials that are prepared by precipitative application comprise generally 1 to 5, more preferably 1 to 4 and especially preferably 1 to 3 active metals.

Irrespective of the number of active metals present in the active composition, in the case of catalytic support materials that are prepared by precipitative application, the composition of the catalytically active components of the active metals is preferably in the range from 5% to 90% by weight, more preferably 10% to 70% by weight and most preferably 15% to 60% by weight, based on the total mass of the catalytic support materials, and where the catalytically active components are calculated as the oxide.

Catalytic support materials that are prepared by precipitative application comprise generally 1 to 5, more preferably 1 to 4 and especially preferably 1 to 3 different added catalyst elements.

Irrespective of the number of added catalyst elements present in the active composition, in the case of catalytic support materials that are prepared by precipitative application, the composition of the catalytically active components of the added catalyst elements is preferably in the range from 1% to 80% by weight, more preferably 5% to 70% by weight and most preferably 10% to 50% by weight, based on the total mass of the catalytic support materials, and where the catalytically active components are calculated as the oxide.

Catalytic support materials that are prepared by impregnation comprise generally 50% to 99% by weight, preferably 75% to 98% by weight and more preferably 90% to 97% by weight of conventional support material.

Catalytic support materials that are prepared by impregnation comprise generally 1 to 5, more preferably 1 to 4 and especially preferably 1 to 3 active metals.

Irrespective of the number of active metals present in the active composition, in the case of catalytic support materials that are prepared by impregnation, the composition of the catalytically active components of the active metals is preferably in the range from 1% to 50% by weight, more preferably 2% to 25% by weight and most preferably 3% to 10% by weight, based on the total mass of the catalytic support materials, and where the catalytically active components are calculated as the oxide.

Catalytic support materials that are prepared by impregnation comprise generally 1 to 4, more preferably 1 to 3 and especially preferably 1 to 2 different added catalyst elements.

Irrespective of the number of added catalyst elements present in the active composition, in the case of catalytic support materials that are prepared by impregnation, the composition of the catalytically active components of the added catalyst elements is preferably in the range from 1% to 50% by weight, more preferably 2% to 25% by weight and most preferably 3% to 10% by weight, based on the total mass of the catalytic support materials, and where the catalytically active components are calculated as the oxide.

Preferred Compositions of Catalytic Support Materials

The catalytic support materials used with particular preference are especially the following compositions:

I)

In a preferred embodiment, the catalytic support materials used are those compositions wherein the catalytically active composition comprises catalytically active components of Zr, Cu and Ni and one or more catalytically active components of Sn, Pb, Bi and In. Compositions of this kind are disclosed, for example, in WO 2008/006749.

In a particularly preferred variant of this embodiment, a composition comprising 10% to 75% by weight, preferably 25% to 65% by weight, more preferably 30% to 55% by weight, of catalytically active components of zirconium, calculated as $ZrO_2$, 1% to 30% by weight, preferably 2% to 25% by weight, more preferably 5% to 15% by weight, of catalytically active components of copper, calculated as CuO, 10% to 70% by weight, preferably 20% to 60% by weight, more preferably 30% to 50% by weight, of catalytically active components of nickel, calculated as NiO, 0.1% to 10% by weight, particularly in the range from 0.2% to 7% by weight, more particularly in the range from 0.4% to 5% by weight, very particularly in the range from 2% to 4.5% by weight, of catalytically active components of one or more metals selected from Sb, Pb, Bi and In, each calculated as $Sb_2O_3$, PbO, $Bi_2O_3$ and $In_2O_3$ respectively, is used.

II)

In a preferred embodiment, the catalytic support material used is a composition wherein the catalytically active composition comprises catalytically active components Zr, Cu, Ni and Co and one or more catalytically active components of Pb, Bi, Sn, Sb and In. Compositions of this kind are disclosed, for example, in WO 2008/006750.

In a particularly preferred variant of this embodiment, a composition comprising 10% to 75% by weight, preferably 25% to 65% by weight, more preferably 30% to 55% by weight, of catalytically active components of zirconium, calculated as $ZrO_2$, 1% to 30% by weight, preferably 2% to 25% by weight, more preferably 5% to 15% by weight, of catalytically active components of copper, calculated as CuO, and 10% to 70% by weight, preferably 13% to 40% by weight, more preferably 16% to 35% by weight, of catalytically active components of nickel, calculated as NiO, 10% to 50% by weight, preferably 13% to 40% by weight, more preferably 16% to 35% by weight, of catalytically active components of cobalt, calculated as CoO, and 0.1% to 10% by weight, particularly in the range from 0.2% to 7% by weight, more particularly in the range from 0.4% to 5% by weight, of catalytically active components of one or more metals selected from Pb, Bi, Sn, Sb and In, each calculated as PbO, $Bi_2O_3$, SnO, $Sb_2O_3$ and $In_2O_3$ respectively, is used.

III)

In a further preferred embodiment, the catalytic support used is those compositions wherein the catalytically active composition comprises catalytically active components of Zr, Ni and Fe and in the range from 0.2% to 5.5% by weight of one or catalytically active components of Sn, Pb, Bi, Mo, Sb and/or P, each calculated as SnO, PbO, $Bi_2O_3$, $MoO_3$, $Sb_2O_3$ and $H_3PO_4$ respectively. Compositions of this kind are disclosed, for example, in WO 2009/080506.

In a particularly preferred variant of this embodiment, a composition comprising 20% to 70% by weight of catalytically active components of zirconium, calculated as $ZrO_2$, 15% to 60% by weight of catalytically active components of nickel, calculated as NiO, and 0.5% to 14% by weight, preferably 1.0% to 10% by weight, more preferably 1.5% to 6% by weight, of catalytically active components of iron, calculated as $Fe_2O_3$, and 0.2% to 5.5% by weight, preferably 0.5% to 4.5% by weight, more preferably 0.7% to 3.5% by weight, of catalytically active components of tin, lead, bismuth, molybdenum, antimony and/or phosphorus, each calculated as SnO, PbO, $Bi_2O_3$, $MoO_3$, $Sb_2O_3$ and $H_3PO_4$ respectively, is used.

IV)

In a further preferred embodiment, the catalytic support used is those compositions wherein the catalytically active composition comprises catalytically active components of Zr, Cu, Ni and in the range from 0.2% to 40% by weight of catalytically active components of cobalt, calculated as CoO, in the range from 0.1% to 5% by weight of catalytically active components of iron, calculated as $Fe_2O_3$, and in the range from 0.1% to 5% by weight of catalytically active components of lead, tin, bismuth and/or antimony, each calculated as PbO, SnO, $Bi_2O_3$ and $Sb_2O_3$ respectively, is used.

Compositions of this kind are disclosed, for example, in WO2009/080508.

In a particularly preferred variant of this embodiment, a composition comprising 20% to 85% by weight, particularly 25% to 70% by weight, more particularly 30% to 60% by weight, of catalytically active components of zirconium, calculated as $ZrO_2$, 0.2% to 25% by weight, particularly 3% to 20% by weight, more particularly 5% to 15% by weight, of catalytically active components of copper, calculated as CuO, 0.2% to 45% by weight, particularly 10% to 40% by weight, more particularly 25% to 35% by weight, of catalytically active components of nickel, calculated as NiO, 0.2% to 40% by weight, preferably 1% to 25% by weight, more preferably 2% to 10% by weight, of catalytically active components of cobalt, calculated as CoO, 0.1% to 5% by weight, preferably 0.2% to 4% by weight, more preferably 0.5% to 3% by weight, of catalytically active components of iron, calculated as $Fe_2O_3$, and 0.1% to 5.0% by weight, particularly 0.3% to 4.5% by weight, more particularly 0.5% to 4% by weight, of catalytically active components of lead, tin, bismuth and/or antimony, each calculated as PbO, SnO, $Bi_2O_3$ and $Sb_2O_3$ respectively, is used.

V)

In a further preferred embodiment, the catalytic support material used is a composition wherein the catalytically active composition comprises catalytically active components Zr, Cu and Ni, and in the range from 1.0% to 5.0% by weight of catalytically active components of cobalt, calculated as CoO, and in the range from 0.2% to 5.0% by weight of catalytically active components of vanadium, niobium, sulfur, phosphorus, gallium, boron, tungsten, lead and/or antimony, each calculated as $V_2O_5$, $Nb_2O_5$, $H_2SO_4$, $H_3PO_4$, $Ga_2O_3$, $B_2O_3$, $WO_3$, PbO and $Sb_2O_3$ respectively.

Compositions of this kind are disclosed, for example, in WO2009/080508.

In a particularly preferred variant of this embodiment, a composition comprising 46% to 65% by weight, particularly 47% to 60% by weight, more particularly 48% to 58% by weight, of catalytically active components of zirconium, calculated as $ZrO_2$, 5.5% to 18% by weight, particularly 6% to 16% by weight, more particularly 7% to 14% by weight, of catalytically active components of copper, calculated as CuO, 20% to 45% by weight, particularly 25% to 40% by weight, more particularly 30% to 39% by weight, of catalytically active components of nickel, calculated as NiO, 1.0% to 5.0% by weight, particularly in the range from 1.5% to 4.5% by weight, more particularly in the range from 2.0% to 4.0% by weight, of catalytically active components of cobalt, calculated as CoO, and 0.2% to 5.0% by weight, particularly 0.3% to 4.0% by weight, more particularly 0.5% to 3.0% by weight of catalytically active components of vanadium, niobium, sulfur, phosphorus, gallium, boron, tungsten, lead and/or antimony, each calculated as $V_2O_5$, $Nb_2O_5$, $H_2SO_4$, $H_3PO_4$, $Ga_2O_3$, $B_2O_3$, $WO_3$, $PbO$ and $Sb_2O_3$ respectively, is used.

VI)

In a further preferred embodiment, the catalytic support material used is a composition wherein the catalytically active composition comprises catalytically active components of Al, Cu, Ni, Co and Sn and in the range from 0.2% to 5.0% by weight of catalytically active components of yttrium, lanthanum, cerium and/or hafnium, each calculated as $Y_2O_3$, $La_2O_3$, $Ce_2O_3$ and $Hf_2O_3$ respectively.

Compositions of this kind are disclosed, for example, in WO 2011/067200.

In a particularly preferred variant of this embodiment, a composition comprising 0.2% to 5.0% by weight, particularly in the range from 0.4% to 4.0% by weight, more particularly in the range from 0.6% to 3.0% by weight, even more particularly in the range from 0.7% to 2.5% by weight, of catalytically active components of tin, calculated as SnO, 10% to 30% by weight, more particularly in the range from 12% to 28% by weight, very particularly 15% to 25% by weight, of catalytically active components of cobalt, calculated as CoO, 15% to 80% by weight, particularly 30% to 70% by weight, more particularly 35% to 65% by weight, of catalytically active components of aluminum, calculated as $Al_2O_3$, 1% to 20% by weight, particularly 2% to 18% by weight, more particularly 5% to 15% by weight, of catalytically active components of copper, calculated as CuO, and 5% to 35% by weight, particularly 10% to 30% by weight, more particularly 12% to 28% by weight, very particularly 15% to 25% by weight, of catalytically active components of nickel, calculated as NiO, 0.2% to 5.0% by weight, particularly in the range from 0.4% to 4.0% by weight, more particularly in the range from 0.6% to 3.0% by weight, even more particularly in the range from 0.7% to 2.5% by weight, of catalytically reactive components of yttrium, lanthanum, cerium and/or hafnium, each calculated as $Y_2O_3$, $La_2O_3$, $Ce_2O_3$ and $Hf_2O_3$ respectively, is used.

VII)

In a further preferred embodiment, the catalytic support material used is a composition that is prepared by applying a solution (L) comprising tin nitrate and at least one complexing agent to the support, where the solution (L) does not comprise any solids or comprises a solids content of not more than 0.5% by weight, based on the total mass of dissolved components, and the solution (L) additionally comprises at least one further nickel salt, cobalt salt and/or copper salt, more preferably nickel nitrate, cobalt nitrate and/or copper nitrate.

Compositions of this kind are disclosed, for example, in WO 2013/072289.

In a preferred variant of this embodiment, a composition comprising 0.2% to 5% by weight of catalytically active components of tin, calculated as SnO, 15% to 80% by weight of catalytically active components of aluminum, calculated as $Al_2O_3$, 1% to 20% by weight of catalytically active components of copper, calculated as CuO, 5% to 35% by weight of catalytically active components of nickel, calculated as NiO, and 5% to 35% by weight of catalytically active components of cobalt, calculated as CoO, is used.

In a very particularly preferred variant of this embodiment, compositions having the aforementioned composition are obtained by precipitating soluble compounds of Co and Sn onto a finely dispersed support material, where the soluble compound is Sn nitrate and the precipitative application is effected in the presence of a complexing agent. The soluble compound of Co is preferably Co nitrate.

The precipitative application is further preferably effected in the presence of at least one further soluble compound of an added catalyst element, preferably a soluble compound of Cu and/or Ni. Further preferably, the added catalyst elements are likewise used in the form of their nitrates or nitrosylnitrates.

The complexing agent is preferably selected from the group consisting of glycolic acid, lactic acid, hydracrylic acid, hydroxybutyric acid, hydroxyvaleric acid, malonic acid, mandelic acid, citric acid, sugar acids, tartronic acid, tartaric acid, oxalic acid, malonic acid, maleic acid, succinic acid, glutaric acid, adipic acid, glycine, hippuric acid, EDTA, alanine, valine, leucine or isoleucine.

The support material is preferably aluminum oxide or zirconium oxide or a mixture thereof.

Shape and Geometry of the Support Materials Used

The support material is preferably used in the form of powder or spall or in the form of shaped bodies.

If the support material is used in the form of powder or spall, the median diameter of the particles $d_{50}$ is generally in the range from 50 to 2000 μm, preferably 100 to 1000 μm and more preferably 300 to 700 μm. The standard deviation of the particle diameter is generally in the range from 5% to 200%, preferably 10% to 100% and especially preferably 20% to 80% of the median diameter $d_{50}$.

In a particularly preferred embodiment, the median diameter $d_{50}$ of the particles of the powder or spall used is preferably in the range from 1 to 500 μm, preferably 3 to 400 μm and more preferably 5 to 300 μm. The standard deviation of the particle diameter is generally in the range from 5% to 200%, preferably 10% to 100% and especially preferably 20% to 80% of the median diameter $d_{50}$.

However, the support materials can also preferably be used in the form of shaped bodies in the process of the invention.

Suitable shaped bodies are shaped bodies having any geometry or shape. Preferred shapes are tablets, rings, cylinders, star extrudates, wagonwheels or spheres, particular preference being given to tablets, rings, cylinders, spheres or star extrudates. Very particular preference is given to the cylinder shape.

In the case of spheres, the diameter of the sphere shape is preferably 20 mm or less, more preferably 10 mm or less, even more preferably 5 mm or less and especially preferably 3 mm or less.

In a preferred embodiment, in the case of spheres, the diameter of the sphere shape is preferably in the range from 0.1 to 20, more preferably 0.5 to 10 mm, even more preferably 1 to 5 mm and especially preferably 1.5 to 3 mm.

In the case of strands or cylinders, the ratio of length: diameter is preferably in the range from 1:1 to 20:1, more preferably 1:1 to 14:1, even more preferably in the range from 1:1 to 10:1 and especially preferably in the range from 1:2 to 6:1.

The diameter of the strands or cylinders is preferably 20 mm or less, more preferably 15 mm or less, even more preferably 10 mm or less and especially preferably 3 mm or less.

In a preferred embodiment, the diameter of the strands or cylinders is preferably in the range from 0.5 to 20 mm, more preferably in the range from 1 to 15 mm, most preferably in the range from 1.5 to 10 mm.

In the case of tablets, the height h of the tablet is preferably 20 mm or less, more preferably 10 mm or less, even more preferably 5 mm or less and especially preferably 3 mm or less.

In a preferred embodiment, the height h of the tablet is preferably in the range from 0.1 to 20 mm, more preferably in the range from 0.5 to 15 mm, even more preferably in the range from 1 to 10 mm and especially preferably in the range from 1.5 to 3 mm.

The ratio of height h (or thickness) of the tablet to the diameter D of the tablet is preferably 1:1 to 1:5, more preferably 1:1 to 1:2.5 and most preferably 1:1 to 1:2.

The shaped body used preferably has a bulk density (to EN ISO 6) in the range from 0.1 to 3 kg/l, preferably from 1.0 to 2.5 kg/l and especially preferably 1.2 to 1.8 kg/l.

Shaping

Preference is given to using support materials that already have the above-described preferred shape and geometry.

Support materials, especially catalytic support materials that do not have the desired shape and geometry after they have been prepared can be subjected to a shaping step.

In the course of shaping, the support materials are generally conditioned by adjusting them to a particular particle size by grinding.

After the grinding, the conditioned support material can be mixed with further additives, such as shaping aids, for example graphite, binders, pore formers and pasting agents, and processed further to give shaped bodies. Preferably, the support material is mixed only with graphite as shaping aid, and no further additives are added in the course of shaping.

Standard processes for shaping are described, for example, in Ullmann [Ullmann's Encyclopedia Electronic Release 2000, chapter: "Catalysis and Catalysts", pages 28-32] and by Ertl et al. [Ertl, Knözinger, Weitkamp, Handbook of Heterogeneous Catalysis, VCH Weinheim, 1997, pages 98 ff.].

Standard processes for shaping are, for example, extrusion, tabletting, i.e. mechanical pressing, or pelletizing, i.e. compaction by circular and/or rotating movements.

The shaping operation can give shaped bodies with the abovementioned geometry.

The shaping can alternatively be effected by spray-drying a suspension of the support material.

The conditioning or shaping is generally followed by a heat treatment.

The heat treatment is generally effected at a temperature in the range from 250 to 1200° C., preferably 300 to 1100° C. and especially from 500 to 1000° C.

The heat treatment can be effected under any suitable gas atmosphere. The heat treatment is preferably effected in the presence of air, where the proportion by volume of air is preferably in the range from 20% to 100%, more preferably 35% to 90% and especially preferably 30% to 70% by volume.

The heat treatment is generally effected in a muffle furnace, a rotary furnace and/or a belt calcining furnace, where the duration is preferably 1 h or more, more preferably in the range from 1 to 24 h and most preferably in the range from 2 to 12 h.

Preparation of the Catalyst Precursors (Impregnation of Conventional or Catalytic Support Materials)

The catalyst precursors are preferably prepared by contacting conventional or catalytic support material with one or more soluble compounds of the active metals and optionally one or more soluble compounds of the added catalyst elements, where the contacting is preferably effected by soaking or impregnation.

The support materials can be contacted with the soluble compounds of the active metals and added catalyst elements can be contacted with the support materials by the customary processes (A. B. Stiles, Catalyst Manufacture—Laboratory and Commercial Preparations, Marcel Dekker, New York, 1983), for example by applying a salt of the active metals or added catalyst elements in one or more impregnation stages.

Useful salts of the active metals or of the added catalyst elements generally include water-soluble salts such as the carbonates, nitrates or nitrosylnitrates, carboxylates, especially carboxylates, preferably the nitrates or nitrosylnitrates and acetates and most preferably the nitrates or nitrosylnitrates of the corresponding active metals or added catalyst elements, which are generally converted at least partly to the corresponding oxides or mixed oxides under the conditions of the calcination.

The contacting can also be effected by the "incipient wetness method", in which the support material is moistened with the impregnation solution up to a maximum of saturation, according to its water absorption capacity, or the support material is sprayed with the impregnation solution. Alternatively, impregnation may take place in supernatant solution.

In the case of multistage impregnation processes, it is appropriate to dry between individual impregnation steps. Multistage impregnation should be employed advantageously when the support material is to be contacted with salts in a relatively large amount.

For application of multiple active metals and/or added catalyst elements and/or basic elements to the support material, the impregnation can be effected simultaneously with all salts or in any sequence of the individual salts in succession.

Preferred conventional support materials are support materials comprising the added catalyst elements Al and Zr or mixtures thereof.

In a very particularly preferred embodiment, the soluble compounds of the active metals that are contacted with the support material are used partly or completely in the form of their nitrates or nitrosylnitrates. Most preferably, soluble compounds of the active metals used are exclusively the nitrates or nitrosylnitrates of the active metals.

It is also preferable that the soluble compounds of the added catalyst elements are used partly or completely in the form of their nitrates or nitrosylnitrates. Most preferably, the soluble compounds of the added catalyst elements used are exclusively the nitrates or nitrosylnitrates of the added catalyst elements.

In an especially preferred embodiment, the soluble compounds of the active metals and added catalyst elements used, with which the support material is contacted, are exclusively the corresponding nitrates or nitrosylnitrates.

In a further preferred embodiment, the support materials used are catalytic support materials comprising, as active metals, one or more active metals selected from the group consisting of Ru, Co, Sn, Cu and Ni. More preferably, the support materials used are catalytic support materials comprising, as active metals, one or more active metals selected from the group consisting of Co, Sn, Cu and Ni.

It is further preferable that the catalytic support materials comprise one or more added catalyst elements selected from the group consisting of Zr and Al.

It is most preferable to use the aforementioned preferred compositions as catalytic support materials.

The support materials may be used, for example, in the form of spall, powders or shaped bodies, such as strands, tablets, spheres or rings.

Preference is given to using support materials that already have the above-described preferred shape and geometry (see section "Shape and geometry of the support materials").

The content of soluble compounds of the active metals with which the support material is contacted, for each active metal, is preferably in the range from 0.1% to 50% by weight, preferably 1% to 40% by weight and more preferably 2% to 15% by weight.

In a particularly preferred embodiment, at least one active metal with which the support material is impregnated is Ru. It is further preferable that, in this embodiment, Ru is used in the form of Ru nitrosylnitrate.

In a further very particularly preferred embodiment, support materials are impregnated with Ru and Co by impregnating the support material simultaneously or successively with a soluble Ru compound and a soluble Co compound, preferably using both Ru and Co in the form of their nitrates or nitrosylnitrates.

The Ru content of the solutions with which the support material is contacted is typically in the range from 0.1% to 50% by weight, preferably 1% to 40% by weight and more preferably 2% to 15% by weight.

The Co content of the solutions with which the support material is contacted is typically in the range from 0.1% to 20% by weight, preferably 0.1% to 5% by weight and more preferably 0.15% to 2% by weight.

The contacting of the support material with the soluble compounds of Co and Ru increases the proportion of Ru in the catalyst precursor by about 0.1% to 5% by weight, preferably 0.5% to 4% by weight and most preferably by 1% to 3% by weight, and increases the proportion of Co in the catalyst precursor by about 0.1% to 5% by weight, preferably 0.5% to 3% by weight and most preferably by 1% to 2% by weight, based in each case on the total mass of the catalyst precursor.

The support material may be contacted simultaneously or successively with a soluble Ru compound and a soluble Co compound.

In a preferred embodiment, the support material is contacted with a solution comprising both a soluble compound of Ru and a soluble compound of Co.

In a further preferred embodiment, the support material is contacted in a first stage with a solution comprising a soluble compound of Ru and subsequently contacted in a second stage with a solution comprising a soluble compound of Co.

In a further preferred embodiment, the support material is contacted in a first stage with a solution comprising a soluble compound of Co and subsequently contacted in a second stage with a solution comprising a soluble compound of Ru.

In the case of multistage impregnation processes, the support material can be separated from the impregnation solution, as described below, and dried between the individual impregnation steps. If the contacting with a soluble Ru compound and a soluble Co compound is effected in two or more impregnation steps, it is preferable that the second impregnation directly follows the drying step from the first impregnation step without any calcining after the drying step between the first and second impregnation.

In this embodiment, the support material is preferably alumina, zirconia or a mixture thereof. Particularly in this embodiment, it is also preferable that the support material is a catalytic support material.

Workup of the Catalyst Precursors

The impregnated catalyst precursors obtained by these impregnation methods are typically processed by separating them from the liquid in which the impregnation has been conducted, and washing and drying them.

Separation and Washing:

The impregnated catalyst precursors are generally separated from the liquid in which the catalyst precursors were prepared and washed.

Processes for separating and washing the catalyst precursors are known, for example, from the article "Heterogenous Catalysis and Solid Catalysts, 2. Development and Types of Solid Catalysts", in Ullmann's Encyclopedia of Industrial Chemistry (DOI: 10.1002/14356007.o05_o02).

The wash liquid used is generally a liquid in which the separated catalyst precursor is sparingly soluble but which is a good solvent for impurities adhering to the catalyst, for example precipitant. A preferred wash liquid is water.

In batch preparation, the separation is generally effected with frame filter presses. The washing of the filter residue with wash liquid can be effected here by passing the wash liquid in countercurrent direction to the filtration direction.

In continuous preparation, the separation is generally effected with rotary drum vacuum filters. The washing of the filter residue is typically effected by spraying the filter residue with the wash liquid.

The catalyst precursor can also be separated off by centrifugation. In general, the washing here is effected by adding wash liquid in the course of centrifuging.

Drying

The catalyst precursor separated off is generally dried.

Processes for drying the catalyst precursors are known, for example, from the article "Heterogenous Catalysis and Solid Catalysts, 2. Development and Types of Solid Catalysts", in Ullmann's Encyclopedia of Industrial Chemistry (DOI: 10.1002/14356007.o05_o02).

The drying is effected here at temperatures in the range from preferably 60 to 200° C., especially from 80 to 160° C. and more preferably from 100 to 140° C., where the drying time is preferably 6 h or more, for example in the range from 6 to 24 h. However, depending on the moisture content of the material to be dried, shorter drying times, for example about 1, 2, 3, 4 or 5 h, are also possible.

The washed catalyst precursor that has been separated off can be dried, for example, in chamber ovens, drum driers, rotary kilns or belt driers.

The catalyst precursor can also be dried by spray-drying a suspension of the catalyst precursor.

In a preferred embodiment, the drying is effected at temperatures of 300° C. or less.

Composition of the Catalyst Precursors
Proportion of the Active Composition

The catalyst precursors used in the process are used preferably in the form of catalyst precursors which consist only of catalytically active composition and optionally a shaping aid (such as graphite or stearic acid, for example) if the catalyst precursor is used in the form of shaped bodies.

The proportion of the catalytically active composition based on the total mass of the catalyst precursor is typically 70% to 100% by weight, preferably 80% to 100% by weight, more preferably 90% to 100% by weight, even more preferably 95% by weight to 100% by weight and more preferably 97% by weight to 100% by weight.

Determination of the Composition of the Catalyst Precursors

The composition of the catalyst precursors can be measured by means of known methods of elemental analysis, for example of atomic absorption spectrometry (AAS), of atomic emission spectrometry (AES), of X-ray fluorescence analysis (XFA) or of ICP-OES (Inductively Coupled Plasma Optical Emission Spectrometry).

The concentration figures (in % by weight) of the catalytically active components in the context of the present invention are reported as the corresponding oxide.

The added catalyst elements of group 1 (alkali metals) are calculated as $M_2O$, for example $Na_2O$.

The added catalyst elements of group 2 (alkaline earth metals) are calculated as MO, for example MgO or CaO.

The added catalyst elements of group 13 (boron group) are calculated $M_2O_3$, for example $B_2O_3$ or $Al_2O_3$.

In the carbon group (group 14), Si is calculated as $SiO_2$, Ge as GeO, Sn as SnO and Pb as PbO.

In the nitrogen group (group 15), P is calculated as $H_3PO_4$, As as $As_2O_3$, Sb as $Sb_2O_3$ and Bi as $Bi_2O_3$.

In the group of the chalcogens (group 16), Se is calculated as $SeO_2$ and Te as $TeO_2$.

In the scandium group (group 3), Sc is calculated as $Sc_2O_3$, Y as $Y_2O_3$ and La as $La_2O_3$.

In the titanium group (group 4), Ti is calculated as $TiO_2$, Zr as $ZrO_2$ and Hf as $HfO_2$.

In the vanadium group (group 5), V is calculated as $V_2O_5$, Nb as $Nb_2O_5$ and Ta as $Ta_2O_5$.

In the chromium group (group 6), Cr is calculated as $CrO_2$, Mo as $MoO_3$ and W as $WO_2$.

In the manganese group (group 7), Mn is calculated as $MnO_2$ and Re as $Re_2O_7$.

In the iron group (group 8), Fe is calculated as $Fe_2O_3$, Ru as $RuO_2$ and Os as $OsO_4$.

In the cobalt group (group 9), Co is calculated as CoO, Rh as $RhO_2$ and Ir as $IrO_2$.

In the nickel group (group 10), Ni is calculated as NiO, Pd as PdO and Pt as PtO.

In the copper group (group 11), Cu is calculated as CuO, Ag as AgO and Au as $Au_2O_3$.

In the zinc group (group 12), Zn is calculated as ZnO, Cd as CdO and Hg as HgO.

The concentration figures (in % by weight) of the catalytically active components of the catalyst precursor are each based—unless stated otherwise—on the total mass of the catalyst precursor after the last drying step prior to the reductive calcination.

Composition of the Catalyst Precursors

When support material is not a catalytic support material, the catalyst precursor, irrespective of the number of active metals and added catalyst elements used, preferably comprises:
0.01% to 20% by weight of active metals; and
80% to 99.99% by weight of added catalyst elements; and more preferably
0.1% to 10% by weight of active metals; and
90% to 99.9% by weight of added catalyst elements; and most preferably
1% to 5% by weight of active metals; and
95% to 99% by weight of added catalyst elements.

When the support material is a catalytic support material, the catalyst precursor, irrespective of the number of active metals and added catalyst elements used, preferably comprises:
5% to 95% by weight of active metals; and
5% to 95% by weight of added catalyst elements; and more preferably
10% to 90% by weight of active metals; and
10% to 90% by weight of added catalyst elements; and most preferably
50% to 80% by weight of active metals; and
20% to 50% by weight of added catalyst elements.

Preferred Catalyst Precursor Compositions

In a preferred embodiment, the catalyst precursor comprises:
0.01% to 20% by weight, more preferably 0.1% to 15% by weight and especially preferably 1% to 10% by weight of catalytically active components of Ru, calculated as RuO; and
1% to 50% by weight, more preferably 10% to 45% by weight and especially preferably 20% to 40% by weight of catalytically active components of Co, calculated as CoO; and
0.1% to 5% by weight, more preferably 0.2% to 4% by weight and especially preferably 1% to 3% by weight of catalytically active components of Sn, calculated as SnO.

In a particularly preferred embodiment, the catalyst precursor comprises:
(i) 0.2% to 5% by weight of catalytically active components of Sn, calculated as SnO,
(ii) 1% to 35% by weight of catalytically active components of Co, calculated as CoO,
(iii) 10% to 80% by weight of catalytically active components of Al and/or Zr, calculated as $Al_2O_3$ and $ZrO_2$ respectively;
(iv) 1% to 35% by weight of catalytically active components of Cu and/or 1% to 35% by weight of catalytically active components of Ni, calculated as CuO and NiO respectively; and
(v) 0.01% to 20% by weight of catalytically active components of Ru, calculated as RuO.

In a particularly preferred embodiment, the catalyst precursor comprises:
(i) 0.2% to 5% by weight of catalytically active components of Sn, calculated as SnO,
(ii) 5% to 35% by weight of catalytically active components of Co, calculated as CoO,
(iii) 15% to 80% by weight of catalytically active components of Al and/or Zr, calculated as $Al_2O_3$ and $ZrO_2$ respectively;
(iv) 1% to 20% by weight of catalytically active components of Cu, calculated as CuO,
(v) 5% to 35% by weight of catalytically active components of Ni, calculated as NiO; and (vi) 0.1% to 20% by weight of catalytically active components of Ru, calculated as RuO.

Reductive Calcination

In general, the drying is followed by the reductive calcination of the catalyst precursors in accordance with the invention.

The reductive calcination is conducted in the presence of a reducing gas, especially hydrogen.

In addition, the reactive calcination can be conducted in the presence of an inert gas, preferably nitrogen, helium or argon, where the proportion by volume of reducing gas, especially hydrogen, in mixtures with inert gas is preferably in the range from 1% to 50% by volume, more preferably in the range from 2.5% to 40% by volume and most preferably in the range from 5% to 20% by weight.

It is further preferable to increase the proportion of hydrogen in the mixture with inert gas in a gradual or stepwise manner, for example from 0% by volume of hydrogen to 20% by volume of hydrogen. For instance, in the course of heating, the proportion by volume of hydrogen may be 0% by volume and, on attainment of the calcination temperature, can be increased in one or more stages or gradually to 20% by volume.

The temperature in the reductive calcination is preferably 100 to 400° C., more preferably 150 to 350° C., more preferably 180 to 300° C. and most preferably 200 to 280° C.

It is especially preferable that the temperature in the reductive calcination does not exceed 300° C. In this case, catalysts that give a particularly positive profile of properties with regard to selectivity, activity and the avoidance of unwanted by-products are obtained.

The reductive calcination is generally followed by a passivation, for example as described hereinafter.

The reductive calcination is generally effected in a muffle furnace, a rotary furnace, a shaft reactor, a rotary furnace, a staged furnace, a fluidized bed reactor and/or a belt calcining furnace.

The reductive calcination is preferably effected in a shaft reactor or rotary furnace.

The calcination time in the reductive calcination is preferably 1 h or more, more preferably in the range from 1 to 24 h and most preferably in the range from 2 to 12 h.

More preferably, the reactor in which the catalyst precursor is reductively calcined, as described below, is connected to a denox plant.

Denox Plant

In the preparation of the amination catalysts by reductive calcination, the reductive calcination of the catalyst precursors may form nitrogen oxides that can form explosive mixtures. Nitrogen oxides can form especially when, in the preparation of the catalyst precursors, a catalytic or non-catalytic support material has been contacted with the nitrates or nitrosylnitrates of the active metals or added catalyst elements.

It was therefore also an object of the present invention to provide a process for preparing amination catalysts that meets high safety standards.

The object was achieved in that a denox plant was used in the preparation of amination catalysts.

The object was also achieved by a process for preparing amination catalysts comprising one or more elements selected from Sn and the elements of groups 8, 9, 10 and 11 of the Periodic Table of the Elements, the amination catalyst being obtained by reductive calcination, wherein the reactor in which the reductive calcination is effected is connected to a denox plant.

The preparation of the catalyst precursors and the reductive calcination are preferably effected as already described above, and preference is also given to the variants and embodiments specified as preferred in each case in the present preparation of the amination catalysts.

It is especially preferable to employ the process of the invention for preparation of amination catalysts when a catalytic or noncatalytic support material has been contacted with one or more nitrates or nitrosylnitrates of the active metals or added catalyst elements in the preparation of the catalyst precursors.

In a particularly preferred embodiment, the reactor in which the reductive calcination is effected is connected to a denox plant. This has the advantage that potentially explosive nitrogen oxides formed in the reductive calcination can be destroyed.

The reductive calcination is generally effected, as already described above, in a muffle furnace, a rotary furnace, a shaft reactor, a staged furnace, a fluidized bed reactor and/or a belt calcining furnace.

The reductive calcination is preferably effected in a shaft reactor or rotary furnace.

In a particular configuration of the present invention, the reactor in which the reductive calcination is effected is connected to a denox plant, and so the gas stream is guided from the outlet of the reactor in which the reductive calcination is conducted to the inlet of the denox plant.

In the denox plant, the nitrogen oxides that may be present in the gas stream are generally partially or completely destroyed.

The denox plant may preferably be configured as a gas scrubbing operation or as a selective catalytic reduction.

In the selective catalytic reduction, ammonia is generally mixed into the offgas from the reductive calcination as reducing agent and guided past denox catalysts, for example titanium oxide- and vanadium oxide-containing catalysts. The nitrogen oxides are generally reacted here with ammonia to give water, in the form of water vapor, and nitrogen.

In a preferred embodiment, the ammonia required for the reduction is fed in together with the hydrogen. The proportion by volume of ammonia in the gas stream of reducing and optionally inert gases is typically 5% to 50% by volume, preferably 10% to 40% by volume and more preferably 20% to 30% by volume, based in each case on the overall gas stream which is guided over the catalyst precursor in the reductive calcination.

In a further preferred embodiment, ammonia is not added until beyond the reactor in which the reductive calcination is effected, and upstream of the denox plant.

It is less preferred to supply the ammonia as an aqueous urea solution, since, in this case, a hydrolysis reaction of urea forms ammonia and CO2. The CO2 formed, as a catalyst poison, can reduce the activity of the amination catalysts.

The temperature of the gas stream which is passed over the denox catalysts is preferably 100 to 400° C., more preferably 150 to 350° C., more preferably 180 to 300° C. and most preferably 200 to 280° C. This corresponds essentially to the temperature that is also employed in the reductive calcination, and so generally no further adjustment of the temperature of the gas stream is required before the passage over the denox catalyst.

The water formed in the reduction with ammonia is typically removed from the gas stream beyond the denox catalysts, preferably by condensation or by drying with suitable molecular sieves, and the gas stream is recycled into the reductive calcination in circulation mode, optionally with addition of additional hydrogen.

The denox plant may also be configured as a gas scrubbing operation. In this case, the nitrogen oxide-containing gas stream is generally contacted with a scrubbing liquid. Useful scrubbing liquids generally include basic substances, for example aqueous suspensions or solutions of alkali metal hydroxide, alkali metal carbonates, alkaline earth metal hydroxides, alkaline earth metal carbonates, ammonia and urea. Preference is given to aqueous solutions of alkali metal hydroxides, especially NaOH and KOH, aqueous solutions or suspensions of alkaline earth metal carbonates or alkaline earth metal hydroxides, especially Mg hydroxide, Mg carbonate, Ca hydroxide, Ca carbonate, aqueous solutions of ammonia or aqueous urea solutions.

The scrubbing liquid used may alternatively be an aqueous hydrogen peroxide solution or else water.

The contacting of the nitrogen oxide-containing gas stream is preferably effected in an absorber which may be configured as an exchange scrubber, spray scrubber, column with random packings or trays, jet scrubber, vortex scrubber, rotary scrubber or Venturi scrubber. The absorber is preferably configured as a column with random packings or trays or a spray scrubber. The gas stream is preferably treated with the scrubbing liquid in a column with countercurrent flow. The gas stream is generally fed here into the lower region and the scrubbing liquid into the upper region of the column. In a preferred embodiment, the scrubbing step is conducted in such a way that the nitrogen oxide-containing gas stream is treated in a scrubbing step with the scrubbing liquid at a temperature of 20 to 80° C., preferably 20 to 70° C. and especially 30 to 60° C. The total pressure in the scrubbing step generally corresponds to the pressure at which the reductive calcination is also conducted, preferably 1 bar abs. The exact operating conditions for the scrubbing can be ascertained as a matter of routine by the person skilled in the art.

The scrubbing liquid can be regenerated by membrane methods, heating, expansion to a lower pressure or stripping. After the regeneration process, the scrubbing liquid can be reused.

The gas stream that leaves the denox plant generally has a concentration of nitrogen oxides lower than the concentration that was present in the gas stream upstream of the denox plant. The gas stream depleted of nitrogen oxides, optionally with additions of hydrogen and/or inert gas, can be recycled back into the reductive calcination stage.

The reductive calcination is generally followed by a passivation, for example as described hereinafter.

Passivation

After the reductive calcination, the catalyst is preferably contacted with an oxygen-comprising gas stream such as air or a mixture of air with nitrogen.

This gives a passivated catalyst. The passivated catalyst generally has a protective oxide layer. This protective oxide layer simplifies the handling and storage of the catalyst, such that, for example, the installation of the passivated catalyst into the reactor is simplified.

For passivation, the reductive calcination is followed by contacting with an oxygenous gas, preferably air. The oxygenous gas may be used with additions of inert gases, such as nitrogen, helium, neon, argon or carbon dioxide. In a preferred embodiment, air is used together with nitrogen, where the proportion by volume of air is preferably in the range from 1% to 80%, more preferably 20% to 70% and especially preferably 30% to 60% by volume. In a preferred embodiment, the proportion by volume of air in the mixture with nitrogen is increased gradually from 0% to about 50% by volume.

The passivation is effected preferably at temperatures up to 50° C., preferably up to 45° C. and most preferably up to 35° C.

Activation

Before being contacted with the reactants, a passivated catalyst is preferably reduced by treatment of the passivated catalyst with hydrogen or a hydrogen-comprising gas.

The activation generally removes the protective passivation layer.

The hydrogen is generally used in technical grade purity. The hydrogen can also be used in the form of a hydrogen-comprising gas, i.e. in mixtures with other inert gases, such as nitrogen, helium, neon, argon or carbon dioxide. In a preferred embodiment, hydrogen is used together with nitrogen, where the proportion by volume of hydrogen is preferably in the range from 1% to 50%, more preferably 2.5% to 30% and especially preferably 5% to 25% by volume. The hydrogen stream can also be recycled into the reduction as cycle gas, optionally mixed with fresh hydrogen and optionally after removal of water by condensation.

The activation is preferably effected in a moving or stationary reduction oven.

The catalyst precursor is more preferably activated in a reactor in which the catalyst precursors are arranged as a fixed bed. Particular preference is given to reducing the catalyst precursor in the same reactor in which the subsequent reaction of MEG and/or MEA with NH3 is effected. The catalyst precursor is generally activated at reduction temperatures of 50 to 600° C., especially from 100 to 500° C., more preferably from 150 to 450° C.

The partial hydrogen pressure is generally from 1 to 300 bar, especially from 1 to 200 bar, more preferably from 1 to 100 bar, the pressure figures here and hereinafter relating to the pressure measured in absolute terms.

In a particularly preferred embodiment, the temperature in the activation is in the range in which the reductive calcination was also conducted, namely preferably 100 to 400° C., more preferably 150 to 350° C., more preferably 180 to 300° C. and most preferably 200 to 280° C. When the activation is also conducted within this lower temperature range, amination catalysts having a particularly advantageous profile of properties are obtained.

Reactants

According to the invention, the inventive conversion of ethylene glycol (EG) and/or monoethanolamine (MEA) and ammonia ($NH_3$) is effected in the presence of the reduced or activated amination catalysts in the liquid phase.

Ethylene Glycol

As ethylene glycol is preferably industrial ethylene glycol having a purity of at least 98%, and most preferably ethylene glycol having a purity of at least 99% and most preferably of at least 99.5%.

The ethylene glycol used in the process can be prepared from ethylene obtainable from petrochemical processes. For instance, in general, ethene is oxidized in a first stage to ethylene oxide, which is subsequently reacted with water to give ethylene glycol. The ethylene oxide obtained can alternatively be reacted with carbon dioxide in what is called the omega process to give ethylene carbonate, which can then be hydrolyzed with water to give ethylene glycol. The omega process features a higher selectivity for ethylene glycol since fewer by-products, such as di- and triethylene glycol, are formed.

Ethene can alternatively be prepared from renewable raw materials. For instance, ethene can be formed by dehydration from bioethanol.

Ethylene glycol can also be prepared via the synthesis gas route, for example by oxidative carbonylation of methanol to give dimethyl oxalate and subsequent hydrogenation thereof. Thus, a further possible petrochemical raw material for the preparation of MEG is also natural gas or coal.

MEA

MEA may also be used in the process of the invention.

MEA can, as described above, be prepared by reacting ethylene oxide with ammonia.

Preferably, MEA can be prepared by reacting MEG with ammonia, for example by the process of the invention, by first reacting MEG with ammonia and separating the MEA formed in addition to EDA from EDA and recycling the MEA separated off, optionally together with unconverted MEG, into the preparation process of the invention.

When MEA is used in the process of the invention without MEG, MEA is preferably used with a purity of at least 97%, and most preferably with a purity of at least 98% and most preferably of at least 99%.

When MEA is used together with MEG in the process of the invention, the proportion by weight of MEA in relation to the mass of MEA and MEG is preferably in the range from 0% to 60% by weight, more preferably 10% to 50% by weight and most preferably 20% to 40% by weight.

Ammonia

According to the invention, ethylene glycol and/or monoethanolamine is reacted with ammonia.

The ammonia used may be conventional commercially available ammonia, for example ammonia with a content of more than 98% by weight of ammonia, preferably more than 99% by weight of ammonia, preferably more than 99.5% by weight, in particular more than 99.8% by weight of ammonia.

Hydrogen

The process of the invention is preferably effected in the presence of hydrogen.

The hydrogen is generally used in technical grade purity. The hydrogen can also be used in the form of a hydrogen-comprising gas, i.e. with additions of other inert gases, such as nitrogen, helium, neon, argon or carbon dioxide. Hydrogen-comprising gases used may, for example, be reformer offgases, refinery gases etc., if and as long as these gases do not comprise any catalyst poisons for the catalysts used, for example CO. However, preference is given to using pure hydrogen or essentially pure hydrogen in the process, for example hydrogen having a content of more than 99% by weight of hydrogen, preferably more than 99.9% by weight of hydrogen, more preferably more than 99.99% by weight of hydrogen, especially more than 99.999% by weight of hydrogen.

Reaction in the Liquid Phase

According to the invention, ethylene glycol and/or monoethanolamine are reacted with ammonia and an amination catalyst in the liquid phase.

In the context of the present invention, "reaction in the liquid phase" means that the reaction conditions, such as pressure and temperature, are adjusted such that both ethylene glycol and monoethanolamine are present in the liquid phase and flow around the amination catalyst in liquid form.

The reaction of MEG and/or MEA with ammonia can be conducted continuously or batchwise. Preference is given to a continuous reaction.

Reactors

Suitable reactors for the reaction in the liquid phase are generally tubular reactors. The catalyst may be arranged as a moving bed or fixed bed in the tubular reactors.

Particular preference is given to reacting ethylene glycol and/or monoethanolamine with $NH_3$ in a tubular reactor in which the amination catalyst is arranged in the form of a fixed bed.

If the catalyst is arranged in the form of a fixed bed, it may be advantageous, for the selectivity of the reaction, to "dilute", so to speak, the catalyst in the reactor by mixing it with inert random packings. The proportion of the random packings in such catalyst preparations may be 20 to 80, preferably 30 to 60 and more preferably 40 to 50 parts by volume.

Alternatively, the reaction is advantageously effected in a shell and tube reactor or in a single-stream plant. In a single-stream plant, the tubular reactor in which the reaction is effected may consist of a series connection of a plurality of (e.g. two or three) individual tubular reactors. A possible and advantageous option here is the intermediate introduction of feed (comprising the reactant and/or ammonia and/or $H_2$) and/or cycle gas and/or reactor output from a downstream reactor.

Reaction Conditions

When working in the liquid phase, the MEG and/or MEA plus ammonia are guided simultaneously in liquid phase, including hydrogen, over the catalyst, which is typically in a preferably externally heated fixed bed reactor, at pressures of generally 5 to 30 MPa (50-300 mbar), preferably 5 to 25 MPa, more preferably 2015 to 25 MPa, and temperatures of generally 80 to 350° C., particularly 100 to 300° C., preferably 120 to 270° C., more preferably 130 to 250° C., especially 160 to 230° C.

The partial hydrogen pressure is preferably 0.25 to 20 MPa (2.5 to 200 bar), more preferably 0.5 to 15 MPa (5 to 150 bar), even more preferably 1 to 10 MPa (10 to 100 bar) and especially preferably 2 to 5 MPa (20 to 50 bar).

Input

ME and/or MEA and ammonia are supplied to the reactor preferably in liquid form and contacted in liquid form with the amination catalyst.

Either trickle mode or liquid-phase mode is possible.

It is advantageous to heat the reactants, preferably to the reaction temperature, even before they are supplied to the reaction vessel.

Ammonia is preferably used in 0.90 to 100 times the molar amount, especially in 1.0 to 20 times the molar amount, based in each case on the MEG and/or MEA used.

The catalyst hourly space velocity is generally in the range from 0.05 to 0.5, preferably 0.1 to 2, more preferably 0.2 to 0.6, kg (MEG+MEA) per kg of catalyst and hour.

At the catalyst hourly space velocities stated, the conversion of MEG or MEA is generally in the range from 20% to 75%, preferably in the range from 30% to 60% and most preferably in the range from 35% to 55%.

The water of reaction formed in the course of the reaction, one mole per mole of alcohol group converted in each case, generally has no detrimental effect on the degree of conversion, the reaction rate, the selectivity, or the catalyst lifetime, and is therefore usefully removed from the reaction product—by distillation, for example—only when said product is worked up.

Output

The output from the amination reactor comprises the products of the amination reaction, unconverted reactants, such as ethylene glycol and ammonia, and also hydrogen and water.

As products of the amination reaction, the output from the amination reactor also comprises the corresponding ethanolamines and/or ethyleneamines based on MEG.

The output from the amination reactor preferably comprises MEA and/or EDA.

As products from the amination reaction, the reaction output also preferably comprises higher linear ethyleneamines of the general formula

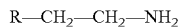

where R is a radical of the formula —(NH—CH$_2$—CH$_2$)$_x$—NH$_2$ where x is an integer in the range from 1 to 4, preferably 1 to 3 and most preferably 1 to 2. Preferably, the reaction output comprises DETA, TETA and TEPA, more preferably DETA and TETA and especially preferably DETA.

As products of the amination reaction, the output from the amination reactor may also comprise higher linear ethanolamines of the formula

where R is a radical of the formula —(NH—CH$_2$—CH$_2$)$_x$—NH$_2$ where x is an integer in the range from 1 to 4, preferably 1 to 3 and most preferably 1 to 2.

One example of a higher linear ethanolamine is AEEA.

As products of the amination reaction, the reaction output may also comprise cyclic ethanolamines of the formula

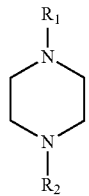

where R$_1$ is a radical of the formula —(CH$_2$—CH$_2$—NH)$_x$—CH$_2$—CH$_2$—OH where x is an integer in the range from 0 to 4, preferably 0 to 3 and more preferably 1 to 2, and R$_2$ is independently or simultaneously either H or a radical of the formula —(CH$_2$—CH$_2$—NH)$_x$—CH$_2$—CH$_2$—OH where x is an integer in the range from 0 to 4, preferably 0 to 3 and more preferably 1 to 2, or a radical of the formula —(CH$_2$—CH$_2$—NH)$_x$—CH$_2$—CH$_2$—NH$_2$ where x is an integer in the range from 0 to 4, preferably 0 to 3 and more preferably 1 to 2. One example of a cyclic ethanolamine is hydroxyethyipiperazine (HEP).

As products of the amination reaction, the reaction output may also comprise cyclic ethyleneamines of the general formula

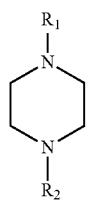

where R$_1$ and R$_2$ are independently or simultaneously either H or a radical of the formula —(CH$_2$—CH$_2$—NH)$_x$—CH$_2$—CH$_2$—NH$_2$ where X is an integer in the range from 0 to 4, preferably 0 to 4 and more preferably 1 to 2.

Examples of cyclic ethyleneamines present in the reaction output are piperazine and AEPIP.

The output preferably comprises 1% to 60% by weight of MEA, 1% to 90% by weight of EDA, 0.1% to 30% by weight of higher cyclic ethyleneamines, such as PIP and AEPIP, 0.1% to 30% by weight of higher linear ethyleneamines, such as DETA, TETA and TEPA.

The output more preferably comprises 10% to 50% by weight of MEA, 25% to 85% by weight of EDA, 0.25% to 10% by weight of cyclic ethyleneamines, such as PIP and AEPIP, 1% to 30% by weight of higher linear ethyleneamines, such as DETA, TETA and TEPA.

The output most preferably comprises 15% to 45% by weight of MEA, 30% to 70% by weight of EDA, 0.5% to 5% by weight of cyclic ethyleneamines, such as PIP and AEPIP, 5% to 25% by weight of higher linear ethyleneamines, such as DETA, TETA and TEPA.

The process of the invention can achieve selectivity quotients SQ of 1.5 or more, preferably 4 or more and more preferably of 8 or more. This means that the product ratio of desired linear ethyleneamines and ethanolamines, such as MEA and EDA, to unwanted cyclic ethyleneamines and unwanted higher ethanolamines, such as PIP and AEEA, can be increased by the process of the invention.

The output is generally worked up, such that the different components are separated from one another.

For this purpose, the reaction output is appropriately decompressed.

The components that are in gaseous form after the decompression, such as hydrogen and inert gases, are generally separated from the liquid components in a gas-liquid separator. The gaseous components can be recycled into the amination reactor individually (after a further workup step) or together.

After hydrogen and/or inert gas has been separated off, the output from the amination reactor optionally comprises ammonia, unconverted ethylene glycol and/or monoethanolamine, water and the amination products.

Preferably, the output from the amination reactor is separated in two separation sequences, where each separation sequence comprises a multistage distillation. Such a workup is described, for example, in EP-B1-198699. Accordingly, in the first separation sequence, water and ammonia are first separated off and, in the second separation sequence, a separation into unconverted MEG, and MEA, EDA, PIP, DETA, AEEA and higher ethyleneamines. In this case, lower- and higher-boiling components relative to the azeotrope of MEG and DETA are first removed and then the mixture that has been concentrated in MEG and DETA is separated by extractive distillation with triethylene glycol (TEG) as selective solvent into a stream comprising MEG and DETA. MEA can be recycled partly or fully into the process of the invention with unconverted MEG, optionally together or separately.

Advantages

In the process of the invention, it is possible to convert MEG and/or MEA with a high selectivity for the linear amination products DETA and EDA, while the selectivity for the cyclic amination product PIP and the higher ethanolamine AEEA is low.

A measure of this effect is the selectivity quotient SQ which is defined as the quotient of the sum total of the selectivities of MEA and EDA and the sum total of the selectivities of PIP and AEEA (SQ=(S(DETA)+S(EDA))/(S(PIP)+S(AEEA)).

The achievement of a high selectivity quotient SQ is industrially advantageous since the market demand for the linear amination products MEA and EDA and their higher homologs, such as DETA and TETA, is higher than the demand for PIP or AEEA.

In addition, the process of the invention forms a lower level of unwanted by-products. Unwanted by-products are, for example, gaseous breakdown products or insoluble or sparingly soluble oligomers and polymers based on MEA and EDA. The formation of such by-products leads to a reduction in the carbon balance and hence to a reduction in the economic viability of the process. The formation of sparingly soluble or insoluble by-products can lead to deposition on the amination catalysts which reduces the activity of the amination catalysts.

The process of the invention likewise leads to a reduction in the amount of N-methylethylenediamine (NMEDA). NMEDA is an unwanted by-product. In many industrial applications, a purity of EDA is specified where the proportion of NMEDA is below 500 ppm by weight.

In addition, it has been found that the catalyst precursors used in the process of the invention have a high activity in the process, and so a favorable space-time yield can be achieved.

Overall, the process of the invention can achieve an advantageous spectrum of properties in relation to overall selectivity, selectivity quotient, activity and the formation of unwanted by-products.

The process of the invention for preparation of amination catalysts has provided a process that meets high safety standards.

The invention is illustrated by the following examples:
Preparation of the Catalyst Precursors

COMPARATIVE EXAMPLE 1

85.62 g of cobalt nitrate hexahydrate were dissolved in about 80 ml of hot demineralized water and 269.75 g of Ru nitrosylnitrate solution (16% by weight of Ru) were added thereto. The solution thus obtained was made up to a total of 371 mL with demineralized water.

The metal salt solution thus obtained was transferred to a spray vessel.

500 g of Al2O3 support (1-2 mm spall) were calcined under an air atmosphere at 900° C.

Thereafter, the maximum water absorption of the support was determined. This was 0.78 mL/g. The spall was impregnated with the metal salt solution prepared beforehand. The amount of the solution corresponds to 95% of the maximum water absorption of the spall.

The spall impregnated with the metal salt solution was then dried at 120° C. in an air circulation drying cabinet for 12 h.

After the drying, the catalyst precursor was oxidatively calcined at 600° C. in the presence of air.

After the oxidative calcination, the catalyst was reduced by passing a gas stream of hydrogen over the catalyst precursor at 200° C. for about 6 hours.

After the reduction, the catalyst was passivated by passing a gas stream of 98 L (STP)/h of N2 and 2 L (STP)/h of air over the catalyst at room temperature. The amount of air was increased gradually, while the amount of N2 was reduced slowly, until 20 L (STP)/h of N2 and 18 L (STP)/h of air were attained. The increase in the amount of air was conducted in such a way that the catalyst temperature did not exceed 35° C.

COMPARATIVE EXAMPLE 2

The catalyst precursor was prepared according to example B3 of WO 2013/072289. Accordingly, the catalyst precursors were oxidatively calcined at a temperature of 450° C. with passage of air. Prior to the reduction of the tablets thus prepared, they were comminuted to 1-2 mm spall.

The catalyst precursor thus obtained was reduced by the following method (see table 1):

TABLE 1

| | Duration (min) | Temperature (° C.) | Nitrogen (L (STP)/h) | Hydrogen (L (STP)/h) | Air (L STP)/h) | Remarks |
|---|---|---|---|---|---|---|
| 1 | 30 min | RT | 100 | — | — | Purge operation at RT |
| 2 | 44 min | 220 | 95 | 5 | — | Heating to 200° C. |
| 3 | 120 min | 220 | 95 | 5 | — | Hold time at 220° C. |
| 4 | 30 min | 280 | 95 | 5 | — | Heating to 280° C. |
| 5 | 15 min | 280 | 95 | 5 | — | Increase in the amount of hydrogen |
| 6 | 15 min | 280 | 90 | 10 | — | Increase in the amount of hydrogen |
| 7 | 15 min | 280 | 80 | 20 | — | Increase in the amount of hydrogen |
| 8 | 15 min | 280 | 70 | 30 | — | Increase in the amount of hydrogen |
| 9 | 15 min | 280 | 60 | 40 | — | Increase in the amount of hydrogen |
| 10 | 15 min | 280 | 50 | 50 | — | Cooling operation to RT |
| 11 | 120 min | 280 | 50 | 50 | — | Hold time at 280° C. |

The reduction was followed by passivation of the catalyst precursor. For this purpose, a stream of 50 L (STP)/h of N2 and 0 L (STP)/h of air was passed over the reduced catalyst precursor. The amount of air was increased gradually, while the amount of N2 was reduced slowly, until 20 L (STP)/h of N2 and 20 L (STP)/h of air were attained. The increase in the amount of air was conducted in such a way that the catalyst temperature did not exceed 35° C.

COMPARATIVE EXAMPLE 3

The catalyst precursor was prepared according to example B3 of WO 2013/072289.

The tablets thus obtained (3*3 mm) were comminuted to 1-2 mm spall. The water absorption of the spall was 0.25 mL/g.

A metal salt solution was prepared. For this purpose, 9.39 g of cobalt nitrate hexahydrate (20.25% by weight of Co) were dissolved in hot water, and 24.58 g of Ru nitrosylnitrate solution were added. The solution thus obtained was made up to 45 mL with demineralized water and transferred to a spray vessel.

The spall was sprayed in an impregnating apparatus with an amount corresponding to 90% of the maximum water absorption of the spall. Thereafter, the catalyst spall was dried in an air circulation drying cabinet at 120° C. for 16 h.

After the drying, the catalyst precursor was oxidatively calcined at 600° C. in the presence of air.

The catalyst precursor thus obtained was reduced by the following method (see table 2):

TABLE 2

|   | Duration (min) | Temperature (° C.) | Nitrogen (L (STP)/h) | Hydrogen (L (STP)/h) | Air (L (STP)/h) | Remarks |
| --- | --- | --- | --- | --- | --- | --- |
| 1 | 30 min | RT | 100 | — | — | Purge operation at RT |
| 2 | 44 min | 220 | 95 | 5 | — | Heating to 220° C. |
| 3 | 120 min | 220 | 95 | 5 | — | Hold time at 220° C. |
| 4 | 30 min | 280 | 95 | 5 | — | Heating to 280° C. |
| 5 | 15 min | 280 | 95 | 5 | — | Increase in the amount of hydrogen |
| 6 | 15 min | 280 | 90 | 10 | — | Increase in the amount of hydrogen |
| 7 | 15 min | 280 | 80 | 20 | — | Increase in the amount of hydrogen |
| 8 | 15 min | 280 | 70 | 30 | — | Increase in the amount of hydrogen |
| 9 | 15 min | 280 | 60 | 40 | — | Increase in the amount of hydrogen |
| 10 | 15 min | 280 | 50 | 50 | — | Cooling operation to RT |
| 11 | 120 min | 280 | 50 | 50 | — | Hold time at 280° C. |

After the reduction, the catalyst precursor was passivated. To this end, a stream of 50 L (STP)/h of N2 and 0 L (STP)/h of air was passed over the catalyst precursor. The amount of air was increased gradually, while the amount of N2 was reduced slowly, until 20 L (STP)/h of N2 and 20 L (STP)/h of air were attained. The increase in the amount of air was conducted in such a way that the catalyst temperature did not exceed 35° C.

Example 1

85.62 g of cobalt nitrate hexahydrate were dissolved in about 80 ml of hot demineralized water and 269.75 g of Ru nitrosylnitrate solution (16% by weight of Ru) were added thereto. The solution thus obtained was made up to a total of 371 mL with demineralized water.

The metal salt solution thus obtained was transferred to a spray vessel.

500 g of Al2O3 support (1-2 mm spall) were calcined under an air atmosphere at 900° C.

Thereafter, the maximum water absorption of the support was determined. This was 0.78 mL/g.

The spall was impregnated with the metal salt solution prepared beforehand. The amount of the solution corresponds to 95% of the maximum water absorption of the spall.

The spall impregnated with the metal salt solution was then dried at 120° C. in an air circulation drying cabinet for 12 h.

After the drying, the catalyst precursor was reductively calcined under the conditions listed in table 1.

TABLE 3

|   | Duration (min) | Temperature (° C.) | Heating rate (° C./min) | Gas flow Nitrogen (L (STP)/h) | Gas flow Hydrogen (L (STP)/h) | Air | Remarks |
| --- | --- | --- | --- | --- | --- | --- | --- |
| 1 | 30 min | RT | none | 100 | — | — | Purge operation at RT |
| 2 | 150 min | 150 | 1 | 95 | 5 | — | Heating to 150° C. |
| 3 | 120 min | 150 | none | 95 | 5 | — | Hold time at 150° C. |
| 4 | 50 min |  | 1 | 95 | 5 | — | Heating to 150° C. |
| 5 | 15 min | 200 | none | 95 | 5 | — | Increase in the amount of hydrogen |
| 6 | 15 min | 200 | none | 90 | 10 | — | Increase in the amount of hydrogen |
| 7 | 15 min | 200 | none | 80 | 20 | — | Increase in the amount of hydrogen |
| 8 | 15 min | 200 | none | 70 | 30 | — | Increase in the amount of hydrogen |
| 9 | 15 min | 200 | none | 60 | 40 | — | Increase in the amount of hydrogen |
| 10 | 15 min | 200 | none | 50 | 50 | — | Cooling operation to RT |
| 11 | 120 min | 200 | none | 50 | 50 | — | Hold time at 200° C. |

After the reductive calcination, the catalyst was passivated by passing a gas stream of 98 L (STP)/h of N2 and 2 L (STP)/h of air over the catalyst at room temperature. The amount of air was increased gradually, while the amount of N2 was reduced slowly, until 20 L (STP)/h of N2 and 18 L (STP)/h of air were attained. The increase in the amount of air was conducted in such a way that the catalyst temperature did not exceed 35° C.

Example 2

A catalyst precursor was prepared according to example B3 of WO 2013/072289.

The tablets thus obtained (3*3 mm) were comminuted to 1-2 mm spall. The water absorption of the spall was 0.30 mL/g.

The catalyst was activated prior to the reaction at 200° C. and 170 bar over a period of 18 h in a 50:50 mixture of hydrogen and nitrogen.

All catalysts were tested under the following conditions:
Temperature: 165° C.
Pressure: 170 bar
H2: 5 L (STP)/h
N2: 10 L (STP)/h
Molar NH3:MEG ratio=10:1
Catalyst hourly space velocity: 0.3 kg/L/h-0.5 kg/L/h
Catalyst volume: 50 mL
The exact conditions are summarized in table 4 below

TABLE 4

| Catalyst | Cat. HSV/ kg/L/h | Conversion/ area % | EDA/ area % | DETA/ area % | AEEA/ area % | PIP/ area % | MEA/ area % | NMEDA + NEEDA + EA/ area % | Tot. sel. (5 main products)/ area % | (EDA + DETA)/ (PIP + AEEA) |
|---|---|---|---|---|---|---|---|---|---|---|
| Comparative ex. 1 | 0.3 | 15.2 | 7.2 | 0.2 | 0.2 | 0.4 | 6.9 | 0.0 | 98.1 | 11.7 |
| Comparative ex. 2 | 0.3 | 27.0 | 11.6 | 0.9 | 0.9 | 1.6 | 11.4 | 0.0 | 97.9 | 5.0 |
| Comparative ex. 3 | 0.3 | 30.3 | 13.5 | 1.2 | 1.1 | 2.6 | 11.1 | 0.0 | 97.4 | 4.0 |
| Example 1 | 0.3 | 46.6 | 20.1 | 2.3 | 2.2 | 5.7 | 11.7 | 2.5 | 90.2 | 2.9 |
| Example 2 | 0.3 | 41.4 | 15.9 | 3.2 | 2.1 | 7.4 | 10.5 | 0.2 | 94.5 | 2.0 |

A metal salt solution was prepared. For this purpose, 20.25 g of cobalt nitrate hexahydrate (20.25% by weight of Co) were dissolved in hot water, and 37.91 g of Ru nitrosylnitrate solution were added. The solution thus obtained was made up to 71 mL with demineralized water and transferred to a spray vessel.

The spall was sprayed in an impregnation apparatus with an amount that corresponds to 95% of the maximum water absorption of the spall. In order to ensure homogeneous uptake of the impregnation solution, the spall was rotated for a further 30 min.

Thereafter, the catalyst spall was dried in an air circulation drying cabinet at 120° C. for 16 h.

The catalyst precursor thus obtained was reductively calcined and passivated as described in example 1.

Catalyst Testing:

The catalysts were tested in a continuously operated parallel plant on the pilot plant scale. The reaction part of the plant consists of eight individual reactors, of which four each are encompassed within one reactor block (heating block). Each individual reactor is a stainless steel tube of length 1.5 m with an internal diameter of 8 mm. The tubes are installed in an electrically heated reactor block consisting of an Al—Mg alloy.

The catalyst was introduced into the reactor in the form of spall (1.5 mm-2 mm) and borne on an inert bed of length about 33 cm consisting of glass beads of size 3 mm.

Above the catalyst bed there is a further, adjoining inert bed of length 15 cm consisting of glass beads of size 3 mm.

The catalyst and the inert bed were fixed in the reactor by a fabric wire of length 1 cm.

Each reactor was operated in straight pass and the flow was from the bottom.

The liquid reactant was supplied from a reservoir with the aid of an HPLC pump. Hydrogen, nitrogen and ammonia were supplied through separate pipelines.

Samples of the liquid reactor outputs were taken from a separator beyond the reactor exit. The reaction outputs were analyzed by gas chromatography.

In comparative example 1, a catalyst precursor (an alumina support material impregnated with Ru and Co) was oxidatively calcined.

Example 1 differs from the comparative example in that the catalyst precursor was calcined not oxidatively, but reductively.

It is found that the reductive calcination drastically increased the conversion. In spite of the high conversion, the selectivity quotient is 2.9, and so the reaction of the invention gave the desired EDA and DETA products to a high degree, and the unwanted PIP and AEEA products were obtained to a small degree. At the same time, only small amounts of unwanted by-products, such as NMEDA, are formed.

In comparative example 2, a the catalyst precursor comprising Ni, Co, Cu and Sn on alumina, after drying, was oxidatively calcined in the presence of air at 450° C.

In comparative example 3, a the oxidatively calcined catalyst precursor from comparative example 2 was post-impregnated with Ru and Co, and the impregnated catalyst precursor thus obtained was oxidatively calcined.

Example 2 differs from example 3 in that the catalyst precursor impregnated with Ru and Co was reductively calcined.

It is found that the reductive calcination drastically increased the conversion. In spite of the high conversion, the selectivity quotient is 2.0, and so the reaction of the invention gave the desired EDA and DETA products to a high degree, and the unwanted PIP and AEEA products were obtained to a small degree. At the same time, only small amounts of unwanted by-products, such as NMEDA, are formed.

A comparison of example 1 and example 2 shows that, in the case of catalyst precursors that are prepared by impregnating a catalytic support material (example 2) rather than a conventional support material (example 1) and then reductively calcined, it is possible to increase the selectivity once again. At the same time, it is possible to lower the amount of unwanted by-products, such as NMEDA.

The invention claimed is:

1. A process for preparing alkanolamines and/or ethyleneamines in a liquid phase, by reacting ethylene glycol and/or monoethanolamine with ammonia in the presence of an amination catalyst comprising one or more active metals selected from Sn and the elements of groups 8, 9, 10 and 11 of the Periodic Table of the Elements, wherein the preparation of the amination catalyst consisting essentially of the following steps:
   (i) preparing a catalyst precursor by contacting a conventional or catalytic support material with one or more soluble compounds of the active metals and optionally one or more soluble compounds of added catalyst elements;
   (i)(a) optionally a work-up step comprising one or more of the steps of separation, washing and drying;
   (ii) reductively calcining the catalyst precursor obtaining in step (i), where the reductive calcination is effected in the presence of hydrogen and the oxygen content in the reductive calcination is less than 0.1% by volume;
   (iii) passivating the reductively calcined catalyst precursor from step (ii);
   (iv) activating the passivated catalyst from step (iii).

2. The process according to claim 1, wherein the catalytic or conventional support material is contacted with the soluble compounds of the active metals and optionally with the soluble compounds of the added catalyst elements by soaking or impregnation.

3. The process according to claim 1, wherein the one or more active metals are selected from the group consisting of Co, Ru, Sn, Ni and Cu.

4. The process according to claim 1, wherein one of the one or more active metals is Ru or Co.

5. The process according to claim 1, wherein the soluble compounds of the active metals that are contacted with the support material are used partly or completely in the form of their nitrates or nitrosylnitrates.

6. The process according to claim 1, wherein the support material comprises Al and/or Zr.

7. The process according to claim 1, wherein the support material is contacted simultaneously or successively with a soluble Ru compound and a soluble Co compound, where the soluble cobalt compound is Co nitrate.

8. The process according to claim 1, wherein the reactor in which the reductive calcination is conducted is a shaft reactor, rotary furnace, staged furnace or fluidized bed reactor.

9. The process according to claim 1, wherein the temperature in the reductive calcination is in the range from 100 to 300° C.

10. The process according to claim 1, wherein the reductive calcination is effected in a reactor connected to a denox plant.

11. The process according to claim 1, that the temperature in the activation is in the range from 100 to 300° C.

12. The process according to claim 1, wherein the reductive calcination is in the presence of hydrogen and an inert gas.

13. The process according to claim 12, wherein hydrogen is present in an amount from 1 to 50% by volume.

14. The process according to claim 12, wherein hydrogen is present in an amount from 2.5% to 30% by volume.

15. The process according to claim 12, wherein hydrogen is present in an amount from 5% to 25% by volume.

16. The process according to claim 1, wherein the catalyst precursor is prepared by coprecipitation and comprise the active metals Ru, Co and Sn.

17. The process according to claim 1, wherein the catalyst precursor comprises:
   0.01% to 20% by weight of catalytically active components of Ru, calculated as RuO;
   1% to 50% by weight of catalytically active components of Co, calculated as CoO; and
   0.1% to 5% by weight of catalytically active components of Sn, calculated as SnO.

18. The process according to claim 1, wherein the catalyst precursor comprises:
   1% to 10% by weight of catalytically active components of Ru, calculated as RuO;
   20% to 40% by weight of catalytically active components of Co, calculated as CoO; and
   1% to 3% by weight of catalytically active components of Sn, calculated as SnO.

19. A process for preparing alkanolamines and/or ethyleneamines in a liquid phase, by reacting ethylene glycol and/or monoethanolamine with ammonia in the presence of an amination catalyst comprising one or more active metals selected from Sn and the elements of groups 8, 9, 10 and 11 of the Periodic Table of the Elements, wherein the preparation of the amination catalyst comprises the following steps:
   (i) preparing a catalyst precursor by contacting a conventional or catalytic support material with one or more soluble compounds of the active metals and optionally one or more soluble compounds of added catalyst elements;
   (i)(a) optionally a work-up step comprising one or more of the steps of separation, washing and drying;
   (ii) reductively calcining the catalyst precursor obtaining in step (i), where the reductive calcination is effected in the presence of hydrogen and the oxygen content in the reductive calcination is less than 0.1% by volume and the reductive calcination is at a temperature of 100 to 280° C.;
   (iii) passivating the reductively calcined catalyst precursor from step (ii);
   (iv) activating the passivated catalyst from step (iii),
   with the proviso that an oxidation calcination is not carried out in the process.

20. The process according to claim 1, which requires the work-up step comprising one or more of the steps of separation, washing and drying.

* * * * *